United States Patent
Lorson et al.

(10) Patent No.: US 12,168,718 B2
(45) Date of Patent: Dec. 17, 2024

(54) THERMOGELLING SUPRAMOLECULAR SPONGE AS SELF-HEALING AND BIOCOMPATIBLE HYDROGEL

(71) Applicant: JULIUS-MAXIMILIANS—UNIVERSITAET WUERZBURG, Wuerzburg (DE)

(72) Inventors: Thomas Lorson, Guentersleben (DE); Robert Luxenhofer, Wuerzburg (DE)

(73) Assignee: Julius-Maximilians-Universitaet Wuerzburg, Wuerzburg (DE)

( * ) Notice: Subject to any disclaimer, the term of this patent is extended or adjusted under 35 U.S.C. 154(b) by 28 days.

(21) Appl. No.: 17/348,157

(22) Filed: Jun. 15, 2021

(65) Prior Publication Data

US 2021/0317267 A1    Oct. 14, 2021

Related U.S. Application Data

(63) Continuation of application No. 16/253,897, filed on Jan. 22, 2019, now abandoned, which is a continuation of application No. PCT/EP2017/062982, filed on May 30, 2017.

(30) Foreign Application Priority Data

Jul. 22, 2016    (EP) ................... 16180838

(51) Int. Cl.
| | | |
|---|---|---|
| *C08G 73/02* | (2006.01) | |
| *A61K 47/59* | (2017.01) | |
| *A61L 27/18* | (2006.01) | |
| *A61L 27/38* | (2006.01) | |
| *A61L 27/44* | (2006.01) | |
| *C08J 3/075* | (2006.01) | |

(52) U.S. Cl.
CPC .......... *C08G 73/0233* (2013.01); *A61K 47/59* (2017.08); *A61L 27/18* (2013.01); *A61L 27/38* (2013.01); *A61L 27/44* (2013.01); *C08J 3/075* (2013.01); *C08J 2379/02* (2013.01); *C08J 2379/04* (2013.01)

(58) Field of Classification Search
CPC ... C08G 73/0233; A61K 47/59; A61K 47/595
See application file for complete search history.

(56) References Cited

U.S. PATENT DOCUMENTS

| | | |
|---|---|---|
| 3,574,784 A | 4/1971 | Litt et al. |
| 5,583,273 A | 12/1996 | Colle ................. C09K 8/52 |
| | | 585/15 |

OTHER PUBLICATIONS

Luxenhofer et al. "Doubly amphiphilic poly(2-oxazoline)s as high-capacity delivery systems for hydrophobic drugs", Biomaterials 31 (2010) 4972-4979 (Year: 2010).*

Debashish Roy et al, "New directions in thermoresponsive polymers", Chemical Society Reviews, GB, (Jan. 1, 2013), vol. 42, No. 17, p. 7214-7243, XP055263788, ISSN 0306-0012, DOI: 10.1039/c3cs35499g.

Lorson: Novel Poly(2-oxazoline) Based Bioinks. Doctoral thesis, Julius-Maximilians—Universität Würzburg—Graduate School of Science and Technology, 2018.

Zahoranová et al: ABA and BAB Triblock Copolymers Based on 2-Methyl-2-oxazoline and 2-n-Propyl-2-oxazoline: Synthesis and Thermoresponsive Behavior in Water. Macromol. Chem. Phys., 2017, vol. 1700031, 12 pages.

* cited by examiner

*Primary Examiner* — James W Rogers
(74) *Attorney, Agent, or Firm* — Laine IP Oy; Mark W. Scott

(57) ABSTRACT

Block copolymers have a general chemical structure of one of the formulas $[A]_n\text{-}[B]_m$ and $[B]_n\text{-}[A]_m$, wherein block [A] is a poly(2-oxazine) and wherein block [B] is a poly(2-oxazoline). The block copolymers have desired thermogelling and rheological properties and are useful as carrier materials for active ingredients such as drugs, cells, proteins, and other active ingredients.

20 Claims, 18 Drawing Sheets

THERMOGELLING SUPRAMOLECULAR SPONGE AS SELF-HEALING AND BIOCOMPATIBLE HYDROGEL

CROSS-REFERENCE TO RELATED APPLICATIONS

This application is a continuation of co-pending U.S. patent application Ser. No. 16/253,897, filed Jan. 22, 2019, which in turn is a continuation, under 35 U.S.C. § 120, of co-pending International Patent Application No. PCT/EP2017/062982, filed May 30, 2017, which designated the United States. This application also claims the priority, under 35 U.S.C. § 119, of European Patent Application No. EP 16180838.1, filed Jul. 22, 2016. The priority applications are each incorporated herein by reference in their entirety.

FIELD OF THE INVENTION

This application is directed to block copolymers with improved thermogelling and rheological properties due to their specific structural composition.

BACKGROUND OF THE INVENTION

Biocompatible polymers that form thermoreversible supramolecular hydrogels have gained great interest recently as so-called bioinks for 3D bioprinting in tissue engineering and biofabrication.

For example, thermogelling polymers find application in food and pharmaceutical technology, biology, and medicine (J. D. Kretlow, S. Young, L. Klouda, M. Wong, A. G. Mikos, *Adv. Mater.* 2009, 21, 3368-3393; N. A. Peppas, J. Z. Hilt, A. Khademhosseini, R. Langer, *Adv. Mater.* 2006, 18, 1345-1360). More recently, they raised great interest as bioinks for three-dimensional (3D) cell culture and bioplotting/biofabrication (R. Censi, W. Schuurman, J. Malda, G. Di Dato, P. E. Burgisser, W. J. A. Dhert, C. F. van Nostrum, P. Di Martino, T. Vermonden, W. E. Hennink, *Adv. Funct. Mater.* 2011, 21, 1833-1842; J. Groll, T. Boland, T. Blunk, J. A. Burdick, D.-W. Cho, P. D. Dalton, B. Derby, G. Forgacs, Q. Li, V. A. Mironov et al., *Biofabrication* 2016, 8, 13001; K. Shi, Y.-L. Wang, Y. Qu, J.-F. Liao, B.-Y. Chu, H.-P. Zhang, F. Luo, Z.-Y. Qian, *Sci. Rep.* 2016, 6, 19077).

Due to diverse requirements, an ideal hydrogel must be available in a consistent quality, a sufficient quantity and with tunable physical and biological properties (T. Jüngst, W. Smolan, K. Schacht, T. Scheibel, J. Groll, *Chem. Rev.* 2016, 116, 1496-1539; S. V. Murphy, A. Atala, *Nature biotechnology* 2014, 32, 773-785; S. Wang, J. M. Lee, W. Y. Yeong, *Int. J. Bioprinting* 2015). In the upcoming field of biofabrication, a shortage of suitable and versatile bioinks represents a major limitation to application and further development to date.

Apart from well-known biological polymers that show thermogelling properties, such as collagen, gelatin, agarose, and others (K. Y. Lee, D. J. Mooney, *Chem. Rev.* 2001, 101, 1869-1880; T. Jüngst, W. Smolan, K. Schacht, T. Scheibel, J. Groll, *Chem. Rev.* 2016, 116, 1496-1539; D. M. Kirchmajer, R. Gorkin III, M. in het Panhuis, *J. Mater. Chem. B* 2015, 3, 4105-4117; N. E. Fedorovich, J. R. de Wijn, A. J. Verbout, J. Alblas, W. J. A. Dhert, *Tissue Eng. Part A* 2008, 14, 127-133) a few synthetic polymer systems also exhibit this property.

In this context, frequently used materials include poly(N-isopropyl-acrylamide) (pNIPAAm) (L. Klouda, *Eur. J. Pharm Biopharm.* 2015, 97, 338-349; H. G. Schild, *Prog. Polym. Sci.* 1992, 17, 163-249; R. A. Stile, W. R. Burghardt, K. E. Healy, *Macromolecules* 1999, 32, 7370-7379) or two members of the family of Pluronics® F127 and P123 (P. Alexandridis, T. Alan Hatton, *Colloids Surf., A* 1995, 96, 1-46). In recent years, these systems have been investigated extensively for biomedical applications (A. V. Kabanov, E. V. Batrakova, S. Sriadibhatla, Z. Yang, D. L. Kelly, V. Y. Alakov, *J. Control. Release* 2005, 101, 259-271), but problems with cytocompatibility have been reported (J. R. Thonhoff, D. I. Lou, P. M. Jordan, X. Zhao, P. Wu, *Brain Res.* 2008, 1187, 42-51).

Even the gelation mechanism of F127 was examined in detail by various techniques, including small angle neutron scattering (SANS). Increasing the temperature beyond the critical temperature (lower critical solution temperature, LCST) leads to aggregation into spherical micelles. At concentrations of ≥5 wt.-%, those micelles arrange in a cubic lattice (K. Mortensen, Y. Talmon, *Macromolecules* 1995, 28, 8829-8834).

Another important class of thermoresponsive polymers comprises polymers obtained from cyclic imino ethers, particularly poly(2-substituted-2-oxazoline)s (POx) and poly(2-substituted-5,6-dihydro-4H-1,3-oxazine)s (in short poly(2-oxazine)s; POzi). These polymers are accessible via living cationic ring-opening polymerization (K. Aoi, M. Okada, *Prog. Polym. Sci.* 1996, 21, 151-208) and can exhibit LCST in aqueous solution where the transition temperature can be tuned over a large temperature range (S. Huber, R. Jordan, *Colloid Polym. Sci.* 2008, 286, 395-402; J.-S. Park, K. Kataoka, *Macromolecules* 2006, 39, 6622-6630; P. Lin, C. Clash, E. M. Pearce, T. K. Kwei, M. A. Aponte, *J. Polym. Sci., Part B: Polym. Phys.* 1988, 26, 603-619).

In the last decade, POx were intensely investigated not only as thermoresponsive material (C. Weber, R. Hoogenboom, U. S. Schubert, *Prog. Polym. Sci.* 2012, 37, 686-714; R. Hoogenboom, H. Schlaad, *Polymers* 2011, 3, 467-488; J.-H. Kim, Y. Jung, D. Lee, W.-D. Jang, *Adv. Mater.* 2016), but also for biomedical applications (A. C. Rinkenauer, L. Tauhardt, F. Wendler, K. Kempe, M. Gottschaldt, A. Traeger, U. S. Schubert, *Macromol. Biosci.* 2015, 15, 414-425; Z. He, L. Miao, R. Jordan, D. S-Manickam, R. Luxenhofer, A. V. Kabanov, *Macromol. Biosci.* 2015, 15, 1004-1020; T. von Erlach, S. Zwicker, B. Pidhatika, R. Konradi, M. Textor, H. Hall, T. Luhmann, *Biomaterials* 2011, 32, 5291-5303; J. Tong, R. Luxenhofer, X. Yi, R. Jordan, A. V. Kabanov, *Mol. Pharm.* 2010, 7, 984-992; K. L. Eskow Jaunarajs, D. G. Standaert, T. X. Viegas, M. D. Bentley, Z. Fang, B. Dizman, K. Yoon, R. Weimer, P. Ravenscroft, T. H. Johnston et al., *Mov. Disord.* 2013, 28, 1675-1682; Z. He, A. Schulz, X. Wan, J. Seitz, H. Bludau, D. Y. Alakhova, D. B. Darr, C. M. Perou, R. Jordan, I. Ojima et al., *J. Control. Release* 2015, 208, 67-75; R. Luxenhofer, A. Schulz, C. Roques, S. Li, T. K. Bronich, E. V. Batrakova, R. Jordan, A. V. Kabanov, *Biomaterials* 2010, 31, 4972-4979; R. Luxenhofer, Y. Han, A. Schulz, J. Tong, Z. He, A. V. Kabanov, R. Jordan, *Macromol. Rapid Commun.* 2012, 33, 1613-1631).

These biomedical applications include covalently cross-linked hydrogels as well (T. R. Dargaville, R. Forster, B. L. Farrugia, K. Kempe, L. Voorhaar, U. S. Schubert, R. Hoogenboom, *Macromol. Rapid Commun.* 2012, 33, 1695-1700; J. N. Haigh, Y.-M. Chuang, B. Farrugia, R. Hoogenboom, P. D. Dalton, T. R. Dargaville, *Macromol. Rapid Commun.* 2016, 37, 93-99; A. M. Kelly, F. Wiesbrock, *Macromol. Rapid Commun.* 2012, 33, 1632-1647; Y. Chujo, K. Sada, T. Saegusa, *Macromolecules* 1990, 23, 2636-2641).

In contrast to POx, POzi received very little attention to date (A. Levy, M. Litt, *J. Polym. Sci., Part B: Polym. Lett.*

1967, 5, 881-886; S. Kobayashi, T. Igarashi, Y. Moriuchi, T. Saegusa, *Macromolecules* 1986, 19, 535-541). Only recently, Bloksma et al. reported on the thermoresponsive behavior of POzi homopolymers (M. M. Bloksma, R. M. Paulus, van Kuringen, Huub P C, F. van der Woerdt, H. M. L. Lambermont-Thijs, U. S. Schubert, R. Hoogenboom, *Macromol. Rapid Commun.* 2012, 33, 92-96).

In particular, in biofabrication, thermoresponsive gels are currently heavily investigated, but new materials that allow the tuning of the response temperature and the rheological properties are urgently needed.

SUMMARY OF THE INVENTION

It is therefore an object of this invention to provide a material with improved thermogelling and rheological properties due to their specific structural composition.

The object with regard to such a material is achieved by a block copolymer, characterized by one of the general chemical structures $[A]_n$-$[B]_m$ or $[B]_n$-$[A]_m$, wherein [A] is a poly(2-oxazine), and wherein [B] is a poly(2-oxazoline), wherein n and m are each in the range of 20 to 300, and wherein n and m have approximately the same value. So the block copolymer with regard to the present invention consists of at least two different blocks [A] and [B] with n or m repetition units each.

Further, a block copolymer is preferred, which is characterized by one of the general chemical structures $[A]_n$-$[B]_m$ or $[B]_n$-$[A]_m$, wherein [A] is a poly(2-oxazine), and wherein [B] is a poly(2-oxazoline), wherein n and m are each in the range of 40 to 300, and wherein n and m have approximately the same value.

For the first time, novel thermogelling block copolymers, comprising a thermoresponsive poly(2-oxazine)s ((POzi)-block) and a hydrophilic poly(2-oxazoline)s ((POx)-block) were synthesized. The rheological properties of aqueous solution of these block copolymers were investigated by viscosimetry and rheology.

Excellent cytocompatibility was shown using NIH 3T3 fibroblasts. Therefore, these novel materials encompass all necessary parameters for use as bioink. As preparing a highly concentrated aqueous polymer solution for freeze drying, the solution, while liquid at 4° C., solidified at the elevated temperature (>25° C.) in laboratory. This is the first case of thermogelling polymers comprising solely poly (cyclic imino ethers).

Depending on the values of n and m (repetition units of the different blocks) the block copolymers according to the present invention undergo thermogelation in different temperature regions. Preferably, the block copolymers according to the present invention undergo thermogelation above 10° C., particularly above 25° C. (for example, block copolymers with the general chemical structure $[A]_{100}$-$[B]_{100}$ or $[B]_{100}$-$[A]_{100}$). Further preferred, the block copolymers according to the present invention undergo thermogelation above 30° C., particularly above 35° C. (for example, block copolymers with the general chemical structure $[A]_{50}$-$[B]_{50}$ or $[B]_{50}$-$[A]_{50}$).

All block copolymers form transparent hydrogels of surprisingly high strength (G'>1000 Pa) and show excellent and rapid shear recovery after stress. The new optical transparent gels have a very suitable and adjustable gelation temperature. The synthesis of the polymers is easy and scalable as well. The gelation process is quite fast. The material is highly cytocompatible, gives relatively stable hydrogels (G'≈4 kPa), but shows pronounced shear thinning. As the formed hydrogels are optically clear, they are suitable for light microscopy.

The term "block copolymer" most simply refers to polymers of at least two different polymer blocks, wherein each polymer block comprises two or more adjacent units of the same kind. In other words, the term "block copolymer" is used herein in accordance with its established meaning in the art to refer to copolymers wherein repeating units of a defined type are organized in blocks [A] and [B].

Preferably, the block copolymers of the present invention are synthesized by a two-stage copolymerization of 2-oxazin and 2-oxazoline. Further preferred, the block copolymers of the present invention are synthesized by a two-stage copolymerization of 2-oxazoline and 2-oxazin. The mechanism showing such a two-stage copolymerization of 2-oxazoline and 2-oxazin is presented in the following general scheme:

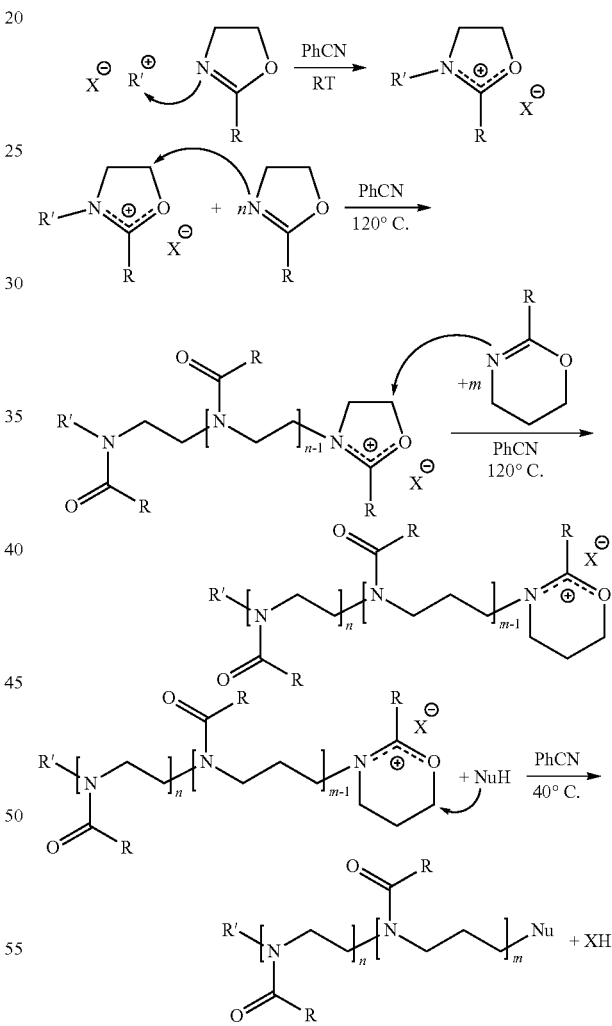

Block A (2-oxazoline as shown in the scheme above) and block B (2-oxazin as shown in the scheme above) can also be interchanged without resulting in a change of mechanical and physico-chemical properties of the synthesized block copolymer.

It is conceivable that the synthesis of the above described polymers is carried out in a one-pot two-step reaction. Below 90° C. only 2-substituted-2-oxazoline should polymerize at a conceivable rate and consequently form block A. By increasing the temperature above 110° C. the reaction of 2-substituted-2-oxazines takes place leading to quasi-block copolymer.

The rest R (of 2-oxazoline and 2-oxazin as well) is preferably an alkyl-group, but of course not limited to this.

Preferably block [A] is chosen of a group containing 2-n-propyl-2-oxazine, 2-cyclopropyl-2-oxazine and 2-butyl-2-oxazine and block [B] is chosen of a group containing 2-methyl-2-oxazoline and 2-ethyl-2-oxazoline. Of course, blocks [A] and [B] are not limited to the above mentioned molecules.

In a preferred embodiment, the block copolymer is characterized by one of the following general chemical structures:

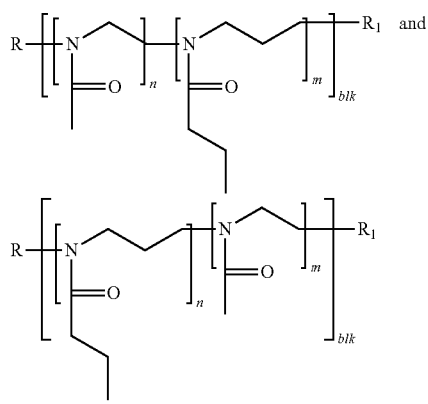

and wherein n is in the range of 20 to 300, wherein m is in the range of 20 to 300, and wherein n and m have the same or approximately the same value.

In a further preferred embodiment, the block copolymer is characterized by one of the following general chemical structures:

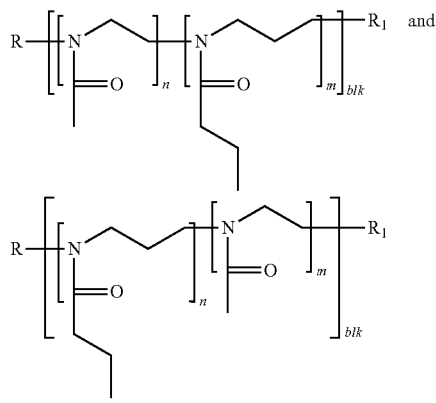

and wherein n is in the range of 40 to 300, wherein m is in the range of 40 to 300, and wherein n and m have the same or approximately the same value.

The end group R in the above shown general chemical structures is introduced by an initiation molecule, starting the polymerization. The final group or termination group $R_1$ is introduced by a termination molecule or termination agent (nucleophile), which stops the polymerization reaction. The initiation molecules as well as the termination molecules may be chosen of a variety of substances. Depending on the selected substances, so depending on the structure of the initiation molecules and the termination molecules, block copolymers with different groups R and $R_1$ are synthesized.

R may be introduced by an initiation molecule chosen of a group containing strong Brønsted, Lewis acids or alkylating agents. In a preferred embodiment, trifluoromethane-sulfonate esters and p-toluenesulfonate esters are employed. Preferably R may be an alkyl group. Further preferred $R_1$ may be introduced by a nucleophilic termination molecule. The nucleophilic termination molecule may be chosen of a group containing hydroxide, Ethyl 4-piperidinecarboxylate, tert-butyl-1-piperazinecarboxylate (1-Boc-Piperazine), 3-mercapto-propionic acid methyl ester, piperazine and its derivates. Preferably, $R_1$ may be a piperidine group.

Of course, the invention is not limited either to the above specified initiation molecules or to the above specified termination molecules. Rather, these molecules and the resulting groups R and $R_1$ shall not effect the gelling behavior of the synthesized block copolymers. In other words, the observed effects with regard to the present invention occur basically independent of the groups R and $R_1$.

In a particular embodiment with regard to the present invention, the block copolymer is characterized by the following chemical structure,

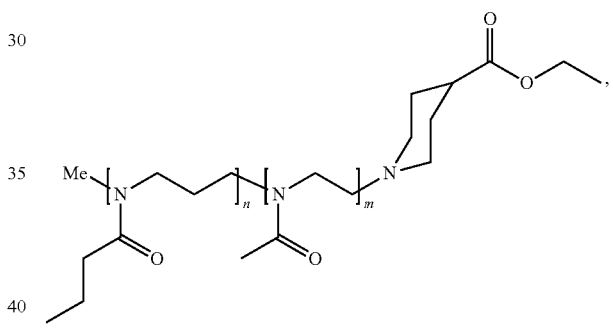

wherein n and m each have a value of 50.

In a further preferred embodiment with regard to the present invention, the block copolymer is characterized by the following chemical structure,

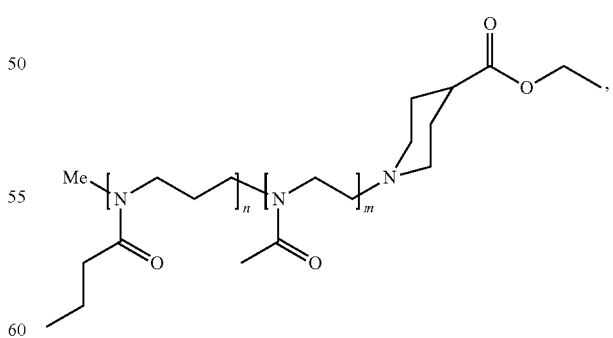

wherein n and m each have a value of 100.

Methyl-P[nPrOzi$_{50}$-b-MeOx$_{50}$]-piperidine-4-carboxylic acid ethyl ester as well as Methyl-P[nPrOzi$_{100}$-b-MeOx$_{100}$]-piperidine-4-carboxylic acid ethyl ester were synthesized by polymerization of 2-n-propyl-2-oxazine (nPrOzi, thermo-responsive POzi block) and 2-methyl-2-oxazoline (MeOx, hydrophilic POx block). The detailed mechanism of the synthesis of the block copolymers is shown later on.

In a further preferred embodiment of the invention the chemical purity of block [A] and/or of block [B] of a block copolymer with one of the general chemical structures $[A]_n$-$[B]_m$ or $[B]_n$-$[A]_m$ is at least 75%, in particular 90%. In detail this means that block [A] comprises at least 75% of a first 2-oxazoline and up to 25% of a second 2-oxazoline or 2-oxazine and/or that block [B] comprise at least 75% of a first 2-oxazine and up to 25% of another 2-oxazine or 2-oxazoline.

The block copolymer is characterized in forming a thermoresponsive hydrogel. Particularly preferred the aqueous solution of the block copolymer forms a thermoresponsive hydrogel. So preferably each block copolymer according to the present invention is characterized by the thermogelling behavior of its aqueous solutions. Gel formation of aqueous polymer solutions only occurs if the concentration exceeds a certain value. With increasing molecular weight, this concentration decreases. For block copolymers with lower molecular weight (as for batches P1 to P5 shown later on), the critical concentration is 20 wt.-% for higher molecular weight is slightly lower at 18 wt.-% (as for batches P1a to P6a shown later on as well).

Depending on the values of n and m, so the repetition units of the block copolymers the gelling temperature may differ. Especially the block copolymers may gel at lower temperatures with increasing chain length, so with higher values of n and m. The block copolymers gel preferably at temperatures above 30° C., particularly above 35° C. (as an example, block copolymers with the general chemical structure $[A]_{50}$-$[B]_{50}$ or $[B]_{50}$-$[A]_{50}$). Further preferred, the block copolymers gel at temperatures above 10° C., preferably above 25° C. (as an example block copolymers with the general chemical structure $[A]_{100}$-$[B]_{100}$ or $[B]_{100}$-$[A]_{100}$).

This gelation behavior as well as the low cytotoxicity, the very good loading capacity, and the resulting rheological properties enable the usage of the respective block copolymers of the present invention in lot of different applications. Advantageously, the block copolymer with regard to the present invention is used as a carrier material for an active agent. Further preferred, the block copolymer is used as a carrier material, wherein the active agent is embedded in carrier material. Preferably, the block copolymer is used as a carrier material for time-delayed disposal of the embedded active agent. The usage of the block copolymer as a carrier material in a drug delivery system is also favored. As well, the use of the block copolymer as a carrier material for cells is preferred. Further, using the block copolymer as a carrier material for proteins is preferred.

The thermogelling in combination with the pronounced isothermal shear-thinning is of advantage for any of these noted applications. Also the hydrogels formed from aqueous solution of the polymers disclosed in the present invention are optically transparent, which is advantageous for said applications.

In the following, materials and methods for preparation and characterization of the used monomers and the resulting polymers for synthesis of different block copolymers are described.

Materials and Methods

All substances for the preparation of monomers and polymers were purchased from Sigma-Aldrich (Steinheim, Germany), Acros (Geel, Belgium) or Fluka (Steinheim, Germany) and were used as received unless otherwise stated. Dulbecco's Modified Eagle Medium (DMEM), fluorescein diacetate (FDA) and propidium iodide (PI) were purchased from Sigma-Aldrich (Schnelldorf, Germany). Penicillin G and streptomycin solution was purchased from Biochrom AG (Berlin, Germany). Fetale bovine serum (FBS) was from Gibco (Darmstadt, Germany). 8-well LabTek chamber slides were from Nunc (Thermo Fisher Scientific, Schwerte, Germany).

96-well plates and 100 mm culture dishes were used from Greiner Bio One (Frickenhausen, Germany). Water soluble tetrazolium (WST-1) was used from Rache (Basel, Switzerland). Methyl trifluoromethylsulfonate (MeOTf), 2-methyl-2-oxazoline (MeOx), benzonitrile (PhCN) and other solvents were dried by refluxing over $CaH_2$ under dry argon atmosphere and subsequent distillation prior to use.

NMR spectra were recorded on a Bruker Fourier 300 ($^1H$ 300.12 MHz) at 298 K, Bruker BioSpin (Rheinstetten, Germany). The spectra were calibrated using the solvent signals (MeOD 3.31 ppm). Gel permeation chromatography (GPC) was performed on a Polymer Standard Service (PSS, Mainz, Germany) system (pump mod. 1260 infinity, RI-detector mod. 1260 infinity, precolumn GRAM 10 µm (50×8 mm), 30 Å PSS GRAM 10 µm (300×8 mm) and 1000 Å PSS GRAM 10 µm (300×8 mm)), with N,N-dimethyl formamide (DMF) (1 g/L LiBr, 313 K, 1 ml/min) as eluent and calibrated against PEG standards. Prior to each measurement, the samples were filtered through a 0.2 µm Teflon filter (Thermo Scientific) to remove particles.

IR spectra were recorded on Jasco (GroB-Umstadt, Germany) FT/IR-4100 equipped with an ATR-unit. Rheology experiments were performed using an Anton Paar (Ostfildem, Germany) Physica MCR 301 utilizing a plate-plate geometry (diameter 25 mm). The rheometer was equipped with a Peltier element. All polymer solutions used for rheology were prepared just before the measurement and were kept in the fridge at approx. 8° C.

At the beginning of each measurement the sample to be characterized equilibrated at 5° C. for 5 min. Afterwards the temperature was raised linearly with 0.66 K/min from 5° C. up to 50° C. The used frequency was 1 Hz and the strain 3%. Dynamic viscosity was measured on an Anton Paar (Graz, Austria) Microviscometer LOVIS 2000M using capillary LOVIS 1.8 equipped with a steel ball (Mat. No. 73109, diameter 1.5 mm, steel 1.4125). Prior to this, density was determined using an Anton Paar (Graz, Austria) Density Meter DMA 4100 M.

Dialysis was performed using Spectra/Por membranes with a molecular weight cutoff (MWCO) of 1 and 4 kDa obtained from neoLab (Heidelberg, Germany).

The SANS measurements were performed at the KWS-1 instrument at the Julich Centre for Neutron Science (JCNS) at Heinz Maier-Leibnitz Zentrum (MLZ) in Garching, Germany (D. Kretlow, S. Young, L. Klouda, M. Wong, A. G. Mikos, Adv. Mater. 2009, 21, 3368-3393; b) N. A. Peppas, J. Z. Hilt, A. Khademhosseini, R. Langer, Adv. Mater. 2006, 18, 1345-1360.)

In all cases a wavelength of $\lambda=7$ Å was used. The sample-detector distances (SDD) of 1.61, 7.61 and 19.61 m were used to cover the complete q range ($q=4\pi \sin(\Theta/2)/\lambda$ is the momentum transfer with $\Theta$ the scattering angle). The wavelength resolution was set to $\Delta\lambda/\lambda=10\%$.

In KWS-1 the detector is a $^6$Li-glass detector with an active area of 60×60 cm². The exposure times were 5, 15 and 35 minutes for the SDDs of 1.61, 7.61 and 19.61 m respectively. The sample was filled into a Hellma cuvette with a light path of 1 mm. This cuvette was placed into a Julabo temperature controlled oven. Dark current correction was carried out using boron carbide.

The scattering of the empty cell was subtracted from the sample scattering, taking the transmissions into account. Poly(methyl methacrylate) was used to bring the data to absolute scale and to determine the detector sensitivity. The resulting intensities were azimuthally averaged. Good agreement was found in the overlap regions of the curves measured at different SDDs. All data reduction steps were performed with the software QtiKWS provided by JCNS.

Subsequent data treatment was carried out the NIST NCNR SANS package for IGOR Pro[2] and procedures written by the authors.

Cell Culture

Murine NIH 3T3 fibroblasts (ATCC-Number CRL-1658, ATCC, Manassas, Va.) were maintained in 100 mm culture dishes in growth medium (DMEM containing 10% heat inactivated FBS, 100 U/mL penicillin G and 100 µg/µL streptomycin) at 37° C. and 5% $CO_2$.

Cell Viability

The lyophilized polymer was dissolved in growth medium at 30 wt.-%. 20.000 NIH 3T3 fibroblasts dispersed in media were incorporated into the polymer stock-solution by gentile mixing with an Eppendorf pipette on ice to yield a 100 µL solution, in which the final polymer concentration was 25 wt.-%. The solution was subsequently added to one well of a preheated (37° C.) 8-well LabTek chambers slide. After incubation for 24 h at 37° C. and 5% $CO_2$, cells were suspended with ice-cold PBS and equally divided in two parts for staining with either 0.01 µg/100 cells FDA or 0.003 µg/100 cells PI dissolved in PBS for 3 min at room temperature as described before (K. Y. Lee, D. J. Mooney, *Chem. Rev.* 2001, 101, 1869-1880).

FDA as non-fluorescent substrate is a viability marker for enzymatic activity and cell-membrane integrity after active conversion to fluorescein ($\lambda_{ex}$=492 nm, $\lambda_{em}$=517 nm) by intracellular esterases in living cells. In contrast PI ($\lambda_{ex}$=540 nm, $\lambda_{em}$=608 nm) does not penetrate intact membranes and intercalates stoichiometrically with nucleic acids in dead cells (T. Jüngst, W. Smolan, K. Schacht, T. Scheibel, J. Groll, *Chem. Rev.* 2016, 116, 1496-1539). The cells were subsequently analysed by flow cytometry on a FACS Calibur system. For detection, a 488 nm Laser was chosen with the emission channel FL2 (585 nm/±21 nm) for PI or the emission channel FL I (530 nm/±15 nm) for FDA, respectively (see FIGS. 18 and 19). A total number of 5000 events were counted with BD CellQuest™ Pro and the geometric mean fluorescence intensity was determined for each condition using Flowing Software (version 2.5.1; Turku Bioimaging).

Distribution of NIH-3T3 Cells

To visualize cells within the thermoreversible gel, the cell pellet of NIH 3T3 fibroblasts was FDA-stained and 20.000 cells were incorporated into a 25 wt.-% polymer solution and added into 37° C. preheated 8-well LabTek chambers slides as described above. FDA stained cells were subsequently analyzed with a Zeiss Observer Z1 epi-fluorescence microscope (Zeiss, Oberkochen, Germany) equipped with a 37° C. incubation chamber. 3D stacks with 1 µm z-stack intervals were taken. Acquired 3D Stacks were analyzed with the ZEN Imaging Software (Zeiss, Oberkochen, Germany).

WST-1 Proliferation Assay

2000 NIH 3T3 fibroblasts were seeded in growth medium in a 96-well-format and incubated overnight at 37° C. and 5% $CO_2$. Dilution concentrations of the 30 wt.-% polymer stock solution were prepared (final polymer concentrations: 10 wt.-%, 5 wt.-%, 1 wt.-%, and 0.02 wt.-%) in growth medium on ice and added to the cells. Cell growth was stimulated for 48 h at 37° C. and 5% $CO_2$.

Before analysis, the cell medium was carefully exchanged and replaced by fresh growth medium. The cells were incubated with WST-1 for 3 h at 37° C. according to the manufacturers instructions. The absorbance of the soluble formazan product was determined at 570 nm using a Spectramax 250 microplate reader from Molecular Devices (Sunnyvale, USA).

Monomer Synthesis

As an example, the synthesis of the monomer 2-n-propyl-2-oxazine (nPrOzi) is shown. 2-n-propyl-2-oxazine was synthesized by an adapted standard procedure (S. Sinnwell, H. Ritter, *Macromol. Rapid Commun.* 2006, 27, 1335-1340), as shown in the following scheme:

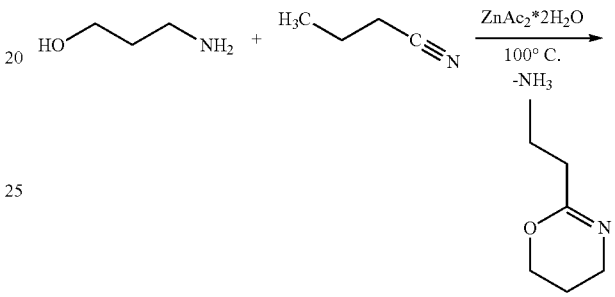

Zincacetate dihydrate (catalyst) was dissolved in propionitrile and 3-amino-1-propanol was added dropwise at room temperature. The reaction mixture was stirred under reflux conditions for at least 24 h. Progression of the reaction was monitored by IR-spectroscopy. After total nitrile consumption the monomer was purified by fractional distillation under inert argon atmosphere to obtain a clear colorless liquid (yield: 363.5 g, 55.5%).

The synthesized 2-n-propyl-2-oxazine (nPrOzi) was characterized by $^1$H-NMR ((300 MHz, δ in ppm, CDCh): 4.09 (t, J=5.5 Hz, $CH_2O$, 2H), 3.31 (t, J=5.9 Hz, $CH_2N$, 2H), 2.05 (t, J=7.8 Hz, $OCCH_2$—$CH_2$, 2H), 1.80 (quintet, J=5.7 Hz, $OCH_2CH_2$, 2H), 1.53 (sextet, J=7.4 Hz, $CCH_2CH_2$, 2H), 0.89 (t, J=7.4 Hz, $CH_3$, 3H)).

2-methyl-2-oxazoline was bought with a purity of 99% and distilled before polymerization under reduced pressure on molecular sieve.

The synthetic procedures for the different block copolymers and the polymerization mechanism are described as follows.

Polymerization of Block Copolymers

The polymerizations and workup procedures were carried out following a general procedure based on previous reports (R. Luxenhofer, A. Schulz, C. Roques, S. Li, T. K. Bronich, E. V. Batrakova, R. Jordan, A. V. Kabanov, *Biomaterials* 2010, 31, 4972-4979; R. Luxenhofer, R. Jordan, *Macromolecules* 2006, 39, 3509-3516). In general, the initiation, so reaction of initiation molecules and the respective monomers already runs at room temperature. The concentration of the initiator molecules depends on the theoretically calculated chain length. The propagation, so the growth of the chain, takes place at about 120° C.

The monomer concentration at the beginning of the reaction is typically laying around 3 mol/l. The chain termination is performed typically at 40° C. and for 4 h at least. In case of monofunctional termination agents typically three equivalents per initiator molecule are inserted. At least ten equivalents are used in the case of bifunctional termination agents, as, for example, piperazine.

As follows, the synthesis of Methyl-Poly[nPrOzi$_{50}$-b-MeOx$_{50}$]-piperidine-4-carboxylic acid ethyl ester (and Methyl-Poly[nPrOzi$_{100}$-b-MeOx$_{100}$]-piperidine-4-carboxylic acid ethyl ester as well) is explained in detail. Methyl-Poly[nPrOzi$_{50}$-b-MeOx$_{50}$]-piperidine-4-carboxylic acid ethyl ester was synthesized by polymerization of 2-n-propyl-2-oxazine (nPrOzi, thermoresponsive POzi block) and 2-methyl-2-oxazoline (MeOx, hydrophilic POx block), as shown in the following mechanism:

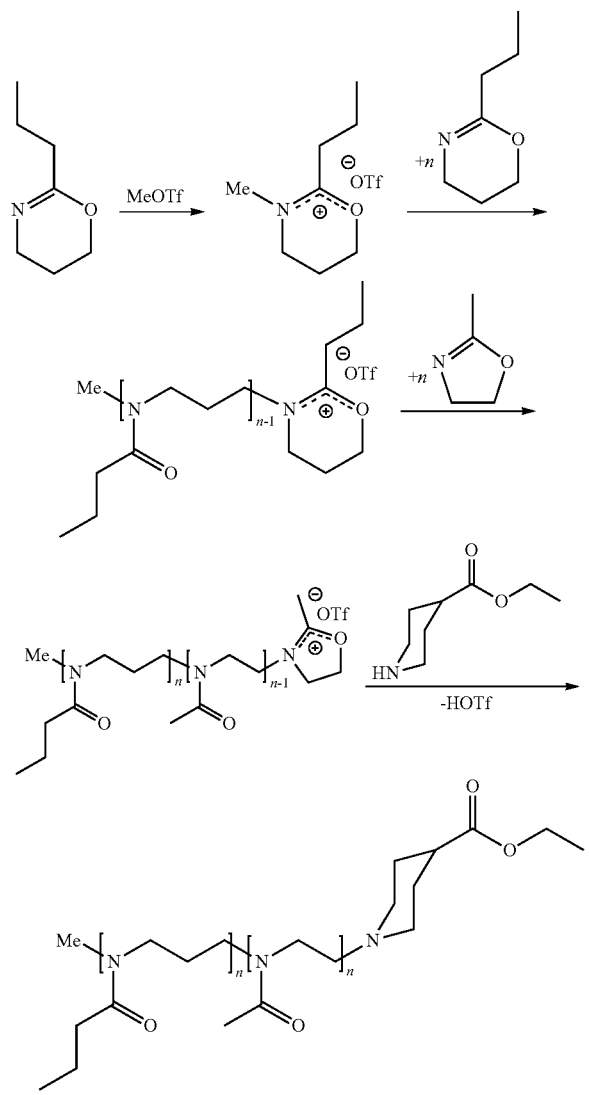

Under dry and inert conditions (glovebox), 276 mg (1.68 mMol, 1 eq) MeOTf and 10.7 g (84.1 mMol, 50 eq) of nPrOzi were added to 17.4 ml dry PhCN in a flame-dried flask at room temperature and polymerized at 100° C. for 4 h. The full monomer conversion was verified by IR-spectroscopy before addition of the monomer for the second block. The mixture was cooled to room temperature, and 7.15 g MeOx (84.0 mMol, 50 eq) dissolved in 21 ml dry PhCN were added. After stirring at 100° C. for 4 h the mixture was cooled to 0° C., and 850 mg (5.41 mMol, 3.2 eq) ethyl isonipecotate were added and the mixture was stirred over night at 40° C.

After cooling to room temperature, potassium carbonate (232 mg, 1.68 mMol, 1 eq) was added, and the mixture was stirred for 5 h. The solvent was removed at reduced pressure from the supernatant after centrifugation, and the flask was placed in a vacuum drying oven at 40° C. and 20 mbar for 2 days. The product was dissolved in ultra-purified water dialyzed overnight using a membrane with a MWCO of 4 kD and freeze-dried (yield: 14.3 g, 79%).

These and various other features of the present invention will become better understood upon the following description of preferred embodiments in conjunction with the accompanying drawings.

Other features which are considered as characteristic for the invention are set forth in the appended claims.

Although the invention is illustrated and described herein as embodied in a thermogelling supramolecular sponge as self-healing and biocompatible hydrogel, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Reference will now be made in detail to the preferred embodiments of the present invention. It is to be understood that the following examples are illustrative only and the present invention is not limited thereto.

Several batches (P1 to P5) of Methyl-P[nPrOzi$_{50}$-b-MeOx$_{50}$]-piperidine-4-carboxylic acid ethyl ester (poly (nPrOzi)-b-poly(MeOx) were analyzed using gel permeation chromatography (GPC) (FIG. 1), temperature dependent rheological properties (FIG. 2) and $^1$H-NMR spectra (FIGS. 3 to 7). The results are first of all summarized in following Table 1:

TABLE 1

Degree of Polymerization (DP) and molar masses (kg/mol) obtained by NMR and GPC of batches P1 to P5.

| | DP $_{theo.}$ | DP$_{exp}$[a] | M$_n$ $_{theo.}$ | Mn[b] | Mw[b] | Đ[b] |
|---|---|---|---|---|---|---|
| P1 | 52/52 | 42/44 | 11.2 | 10.0 | 14.9 | 1.49 |
| P2 | 50/50 | 57/55 | 10.8 | 7.3 | 8.5 | 1.17 |
| P3 | 50/50 | 51/51 | 10.8 | 6.3 | 8.1 | 1.29 |
| P4 | 50/58 | 55/50 | 11.5 | 6.4 | 8.2 | 1.28 |
| P5 | 51/49 | 44/45 | 10.8 | 6.5 | 7.8 | 1.22 |

[a]Determined by end-group analysis ($^1$H NMR spectroscopy in MeOD-d$^4$ (300 MHz, 298 K));
[b]Determined from GPC in DMF with LiBr (1 g/L) at 313 K.

Figure 1:
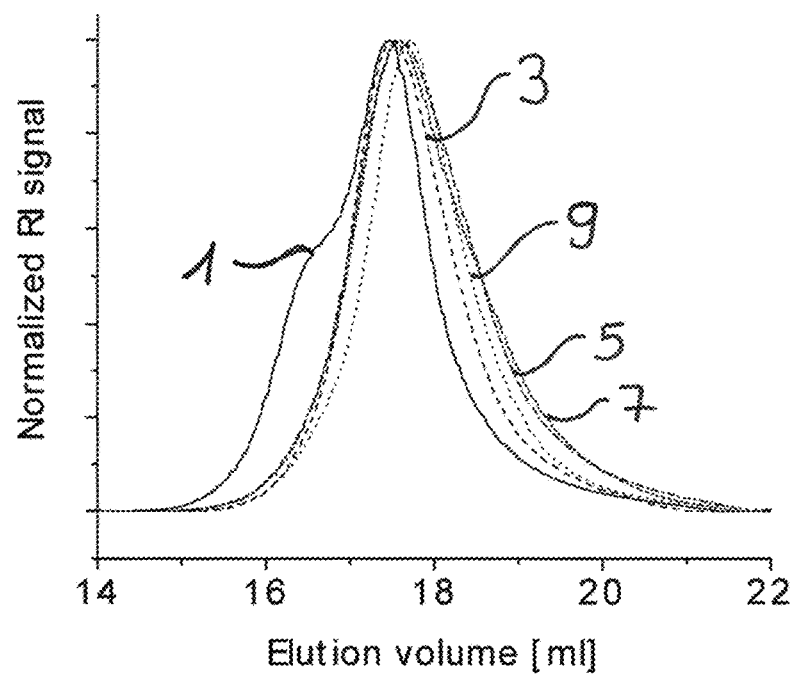
FIG. 1 shows GPC traces for different batches of Methyl-P[nPrOzi$_{50}$-b-MeOx$_{50}$]-piperidine-4-carboxylic acid ethyl ester.

FIG. 1 shows the GPC traces for batches P1 to P5 of Methyl-P[nPrOzi$_{50}$-b-MeOx$_{50}$]-piperidine-4-carboxylic acid ethyl ester, represented by curves 1, 3, 5, 7, 9. The elugrams obtained by GPC appear, with the exception of the first batch P1 (curve 1), nearly monomodal with only minor tailing to lower molar masses. Batch P1 exhibits a significant shoulder at higher molar masses, accordingly, dispersity is highest in this sample (Đ=1.49).

Figure 2:
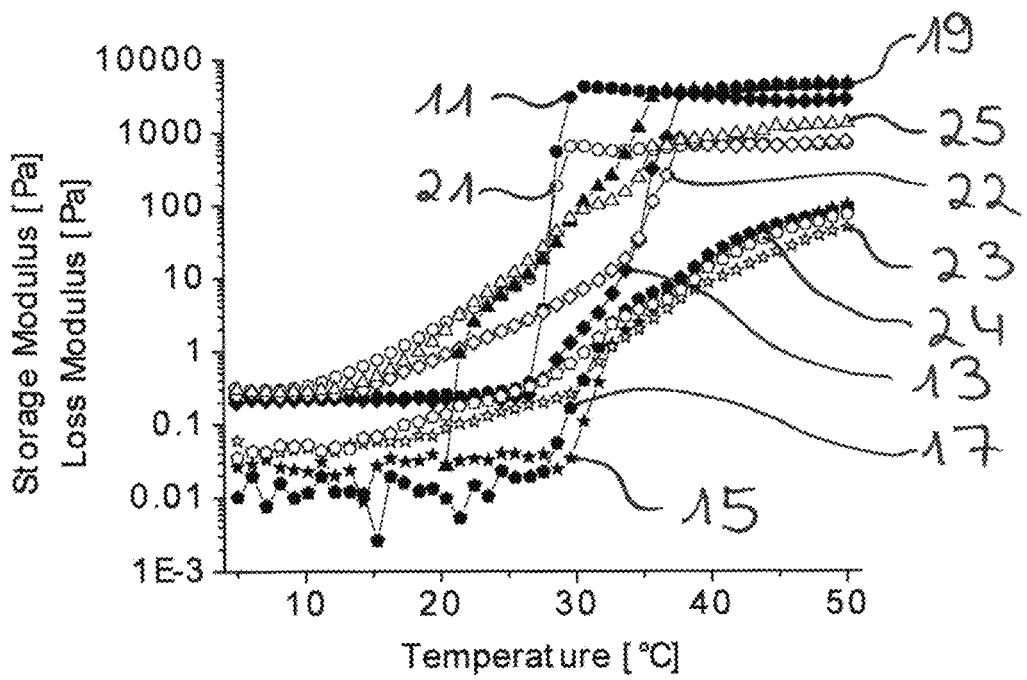
FIG. 2 shows the temperature dependent rheology analysis with storage modulus (G') and loss modulus (G") for 20 wt.-% of Methyl-P[nPrOzi$_{50}$-b-MeOx$_{50}$]-piperidine-4-carboxylic acid ethyl ester.
Figure 3:
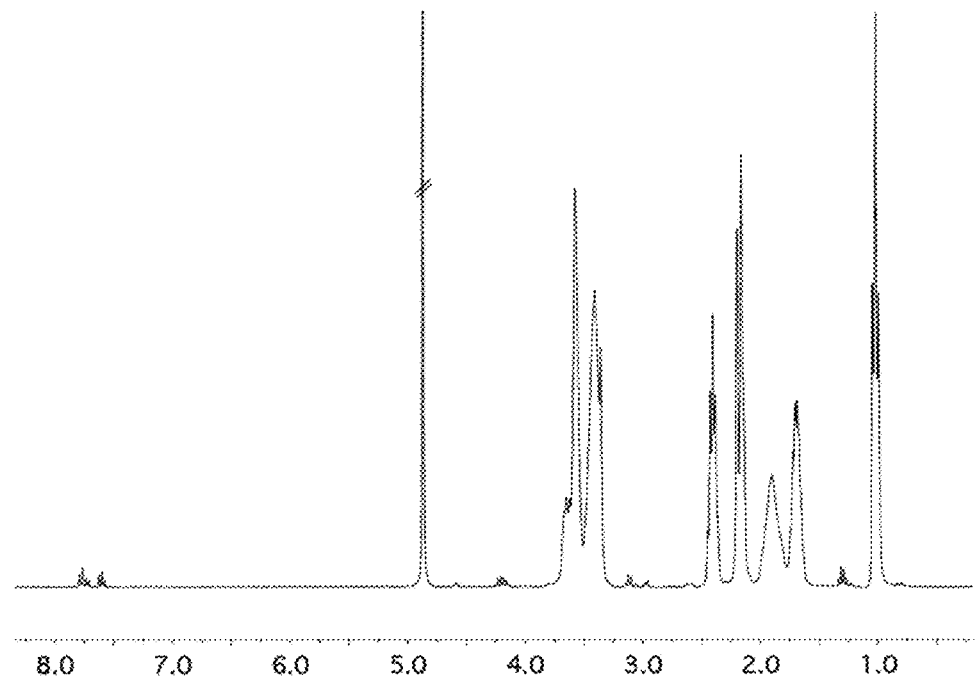
FIG. 3 shows an $^1$H-NMR spectra of batch P1 in methanol-d$^4$ at 298 K of Methyl-P[nPrOzi$_{50}$-b-MeOx$_{50}$]-piperidine-4-carboxylic acid ethyl ester.
Figure 4:
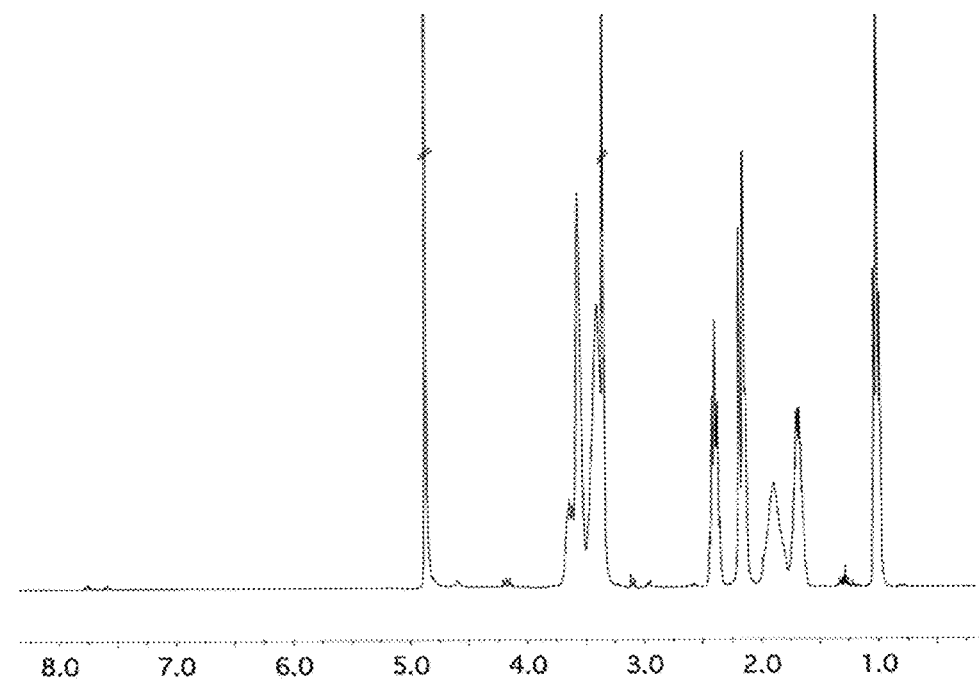
FIG. 4 shows an $^1$H-NMR spectra of batch P2 in methanol-d$^4$ at 298 K of Methyl-P[nPrOzi$_{50}$-b-MeOx$_{50}$]-piperidine-4-carboxylic acid ethyl ester.
Figure 5:
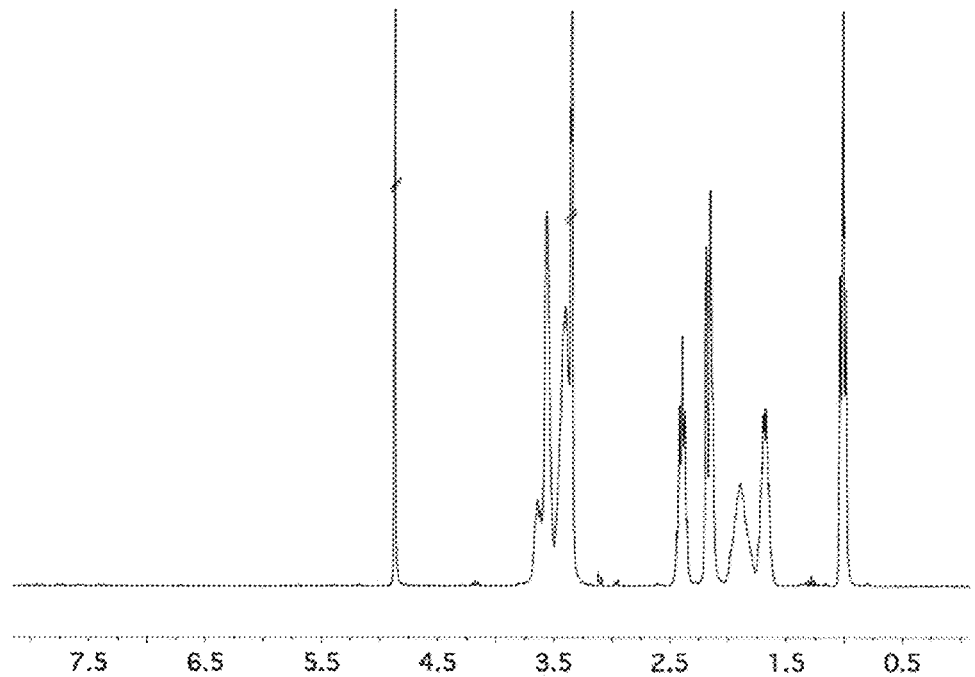
FIG. 5 shows an $^1$H-NMR spectra of batch P3 in methanol-d$^4$ at 298 K of Methyl-P[nPrOzi$_{50}$-b-MeOx$_{50}$]-piperidine-4-carboxylic acid ethyl ester.
Figure 6:
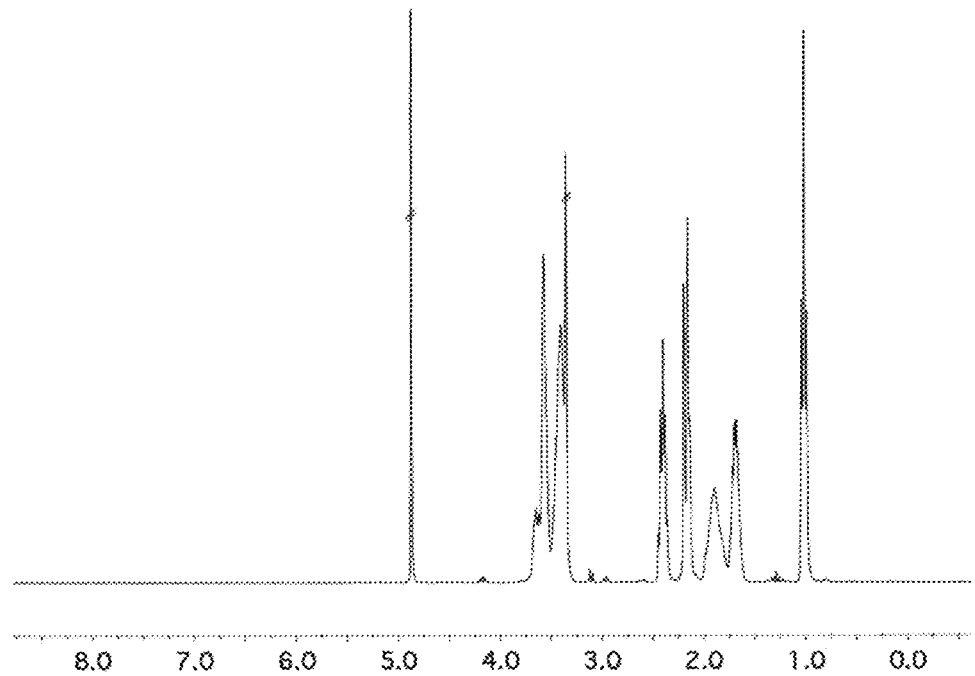
FIG. 6 shows an $^1$H-NMR spectra of batch P4 in methanol-d$^4$ at 298 K of Methyl-P[nPrOzi$_{50}$-b-MeOx$_{50}$]-piperidine-4-carboxylic acid ethyl ester.
Figure 7:
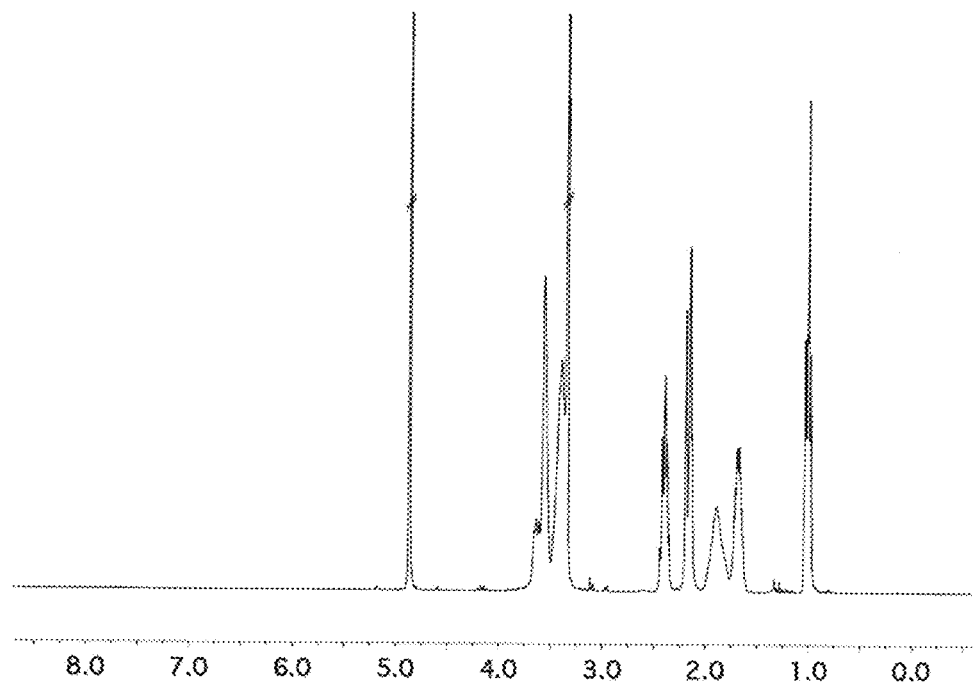
FIG. 7 shows a $^1$H-NMR spectra of batch P5 in methanol-d$^4$ at 298 of Methyl-P[nPrOzi$_{50}$-b-MeOx$_{50}$]-piperidine-4-carboxylic acid ethyl ester.

FIG. 2 shows the temperature dependent rheology with storage modulus (G') and loss modulus (G") for 20 wt.-% of Methyl-P[nPrOzi$_{50}$-b-MeOx$_{50}$]-piperidine-4-carboxylic acid ethyl ester. Storage modulus (G') of batches P1 to P5 is represented by curves 11, 13, 15, 17 and 19 and loss modulus (G") of batches P1 to P5 is represented by curves 21, 22, 23, 24, and 25.

Figure 8:
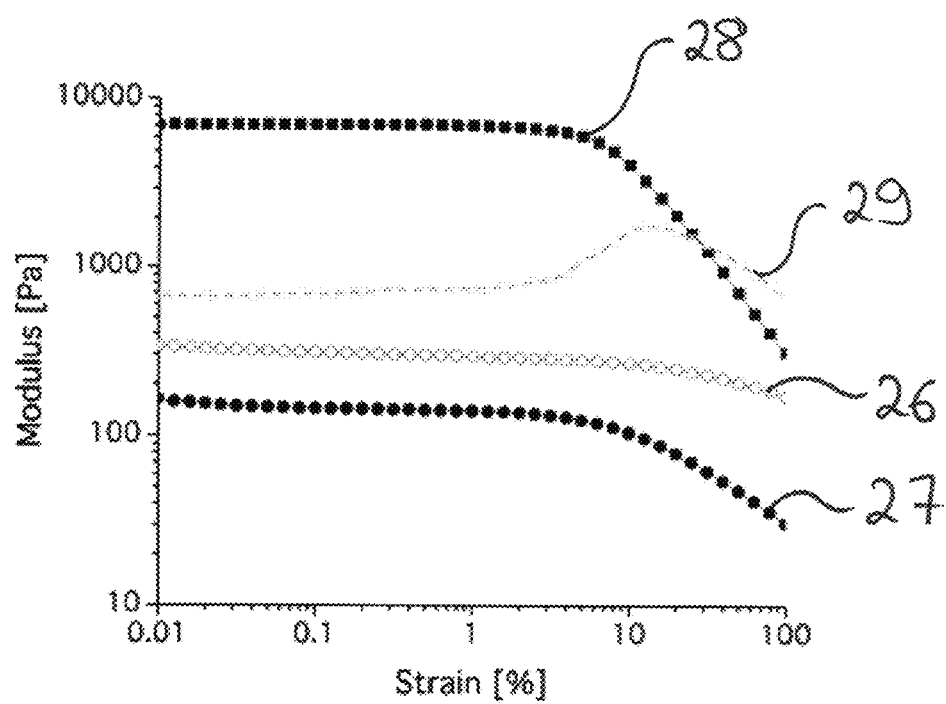
FIG. 8 shows an amplitude sweep used to determine the LVE-range at 10° C. and 50° C. for batch P2.

The rheological properties of aqueous solutions of batch P1 (20 wt.-%, curves 11 and 21 in FIG. 2) were investigated dependent on temperature in the linear viscoelastic range. With regard to this, FIG. 8 shows the amplitude sweep used to determine the LVE-range at 10° C. and 50° C. for batch P2. Curves 26 (G") and 27 (G') show the results at 10° C. and curves 28 (G') and 29 (G") show the results at 50° C. A relatively sharp sol-gel transition at approximately 27° C. was observed. Notably, G" starts to increase at much lower temperature than G' (approximately 13° C.), which corresponds with the cloud point of PnPrOzi as homopolymer (M.

M. Bloksma, R. M. Paulus, van Kuringen, Huub P C, F. van der Woerdt, H. M. L. Lambermont-Thijs, U. S. Schubert, R. Hoogenboom, *Macromol. Rapid Commun.* 2012, 33, 92-96).

After gelation, G' reaches a plateau at about 4 kPa. Therefore, these gels are surprisingly strong compared to many other thermogelling polymers, for which values <1 kPa are more commonly found in the literature (C. Li, N. J. Buurma, I. Haq, C. Turner, S. P. Armes, V. Castelletto, I. W. Hamley, A. L. Lewis, *Langmuir* 2005, 21, 11026-11033; S. Xuan, C.-U. Lee, C. Chen, A. B. Doyle, Y. Zhang, L. Guo, V. T. John, D. Hayes, D. Zhang, *Chem. Mater.* 2016, 28, 727-737). A prominent exception are hydrogels of F127 at 20 wt.-% (approximately 10 kPa) (G. Grassi, A. Crevatin, R. Farra, G. Guamieri, A. Pascotto, B. Rehimers, R. Lapasin, M. Grassi, *J. Colloid Interface Sci.* 2006, 301, 282-290).

Comparing the different batches P1 to P5, it was found that for 20 wt.-% only batches P1 (curves 11 and 21), P2 (curves 13 and 22) and P5 (curves 19 and 25) formed such relatively strong gels (G"/G'=tan δ≈0.2). In contrast, P3 (curves 15 and 23) and P4 (curves 17 and 24) formed gels as evidenced by G'>G", albeit very weak ones (tan δ≈1; G'<0.1 kPa). This was surprising as all batches, in particular batches P2 to P5, appeared very similar from GPC analysis (FIG. 1) and $^1$H-NMR spectra (to be seen in FIGS. 3 to 7).

Batches P3 and P4 only show a somewhat more pronounced low-molecular tailing in the GPC elugrams (FIG. 1). Surprisingly, this minor tailing appears to influence the gelation behaviour very significantly, which emphasizes the problem of batch-to-batch reproducibility in the context of biomaterials research (R. Luxenhofer, *Nanomedicine* 2015, 10, 3109-3119). $^1$H-NMR spectra shown in FIGS. 3 to 7 were in good agreement with the targeted polymer composition. Taking into account the requirements defined by Wang et al. batches P1, P2, and P5 appear suitable for bioprinting (S. Wang, J. M. Lee, W. Y. Yeong, *Int. J. Bioprinting* 2015).

Figure 9:
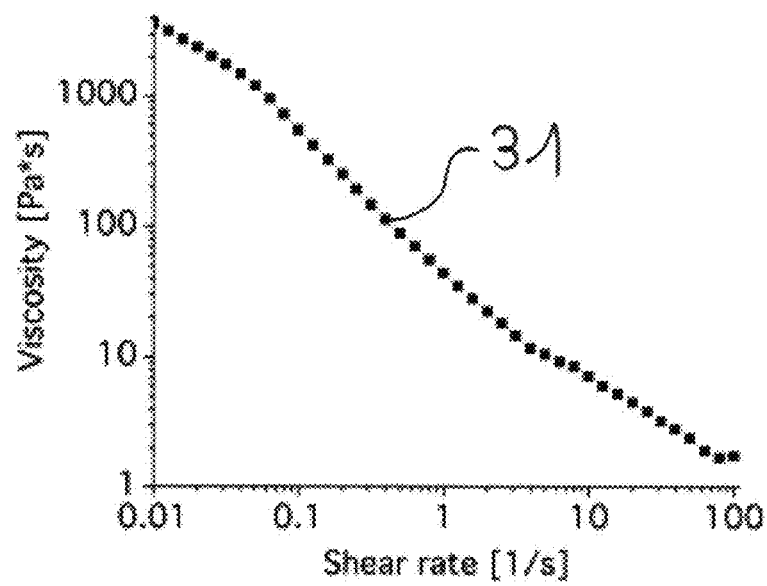
FIG. 9 shows a flow curve at 37° C. for 20 wt.-% of Methyl-P[nPrOzi$_{50}$-b-MeOx$_{50}$]-piperidine-4-carboxylic acid ethyl ester.
Figure 10:
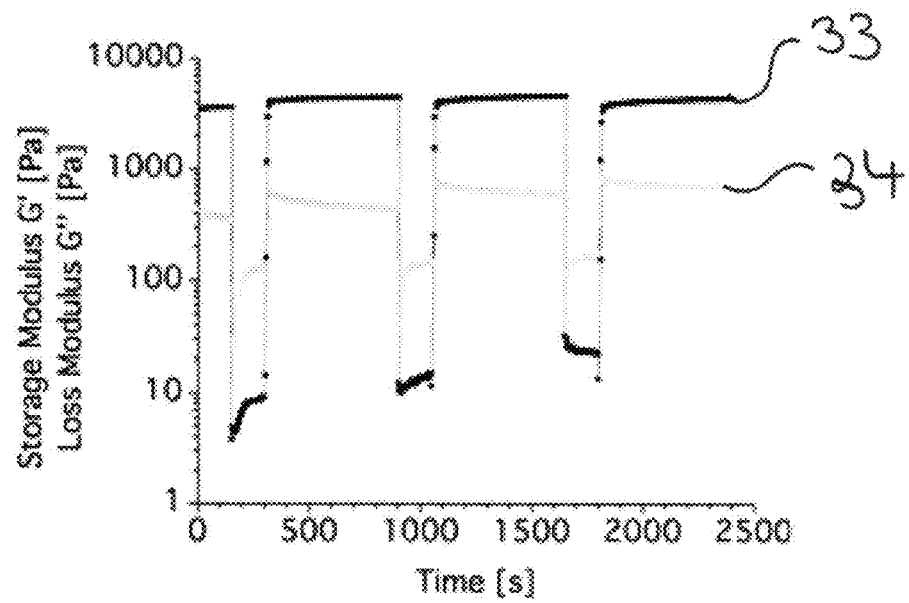
FIG. 10 shows shear recovery at 37° C. for 20 wt.-% of Methyl-P[nPrOzi$_{50}$-b-MeOx$_{50}$]-piperidine-4-carboxylic acid ethyl ester.

In FIG. 9 a flow curve 31 at 37° C. for batch P2 (20 wt.-% of Methyl-P[nPrOzi$_{50}$-b-MeOx$_{50}$]-piperidine-4-carboxylic acid ethyl ester) is shown. A crucial bioink parameter of batch P2 was investigated at 20 wt.-% and 37° C. (D. B. Kolesky, R. L. Truby, A. S. Gladman, T. A. Busbee, K. A. Homan, J. A. Lewis, *Adv. Mater.* 2014, 26, 3124-3130). The viscosity decreased from 4 kPa*s to 1 Pa*s with increasing shear rate from 0.01 s$^{-1}$ to 100 s$^{-1}$. Once the shear-stress stopped, the hydrogel regained strength very rapidly. This can be taken out of FIG. 10, which shows shear recovery at 37° C. for batch P2 (Storage Modulus G', curve 33, Loss Modulus G", curve 34). This combination of pronounced isothermal shear-thinning with rapid recovery is very desirable for bioinks.

Figure 11:
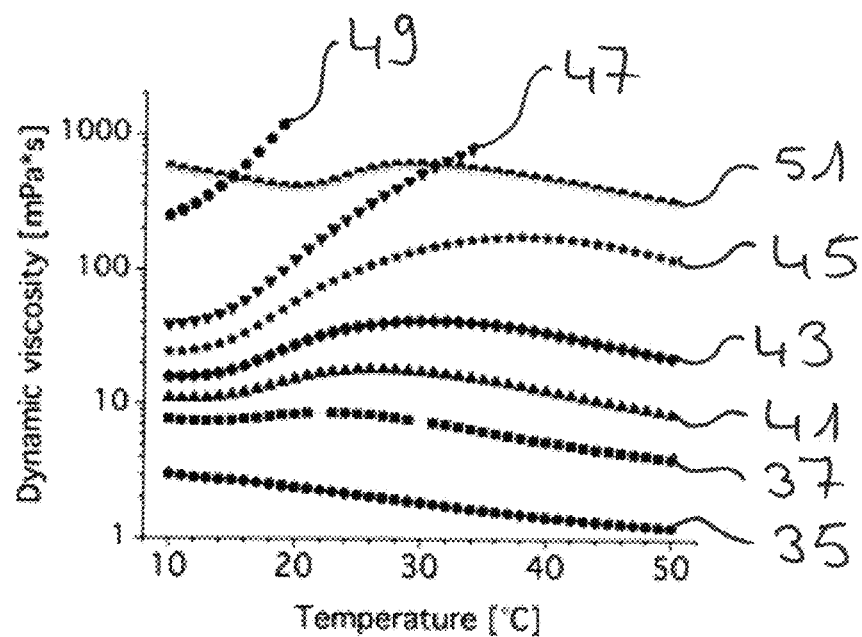
FIG. 11 shows the temperature- and concentration-dependent viscosity of Methyl-P[nPrOzi$_{50}$-b-MeOx$_{50}$]-piperidine-4-carboxylic acid ethyl ester at different concentrations compared with the temperature- and concentration-dependent viscosity of the Poloaxamer F127 at 10 wt.-%.

For a better understanding of the rheological properties of the novel block copolymers, temperature and concentration dependent viscosity of aqueous solutions of P2 were measured (curve 35 (5 wt.-%), curve 37 (10 wt.-%), curve 41 (12.5 wt.-%), curve 43 (15 wt.-%), curve 45 (17.5 wt.-%), curve 47 (20 wt.-%), curve 49 (30 wt.-%) and comparison curve 51 F127 (10 wt.-%). The results can be seen in FIG. 11. It can be seen, that solutions of 20 wt.-% and more (curves 47 and 49 in FIG. 11) are gelling with increasing temperature. Below the LCST (lower critical solution temperature) of PnPrOzi a transparent solution of relatively low viscosity was observed at all concentrations.

Figure 21:
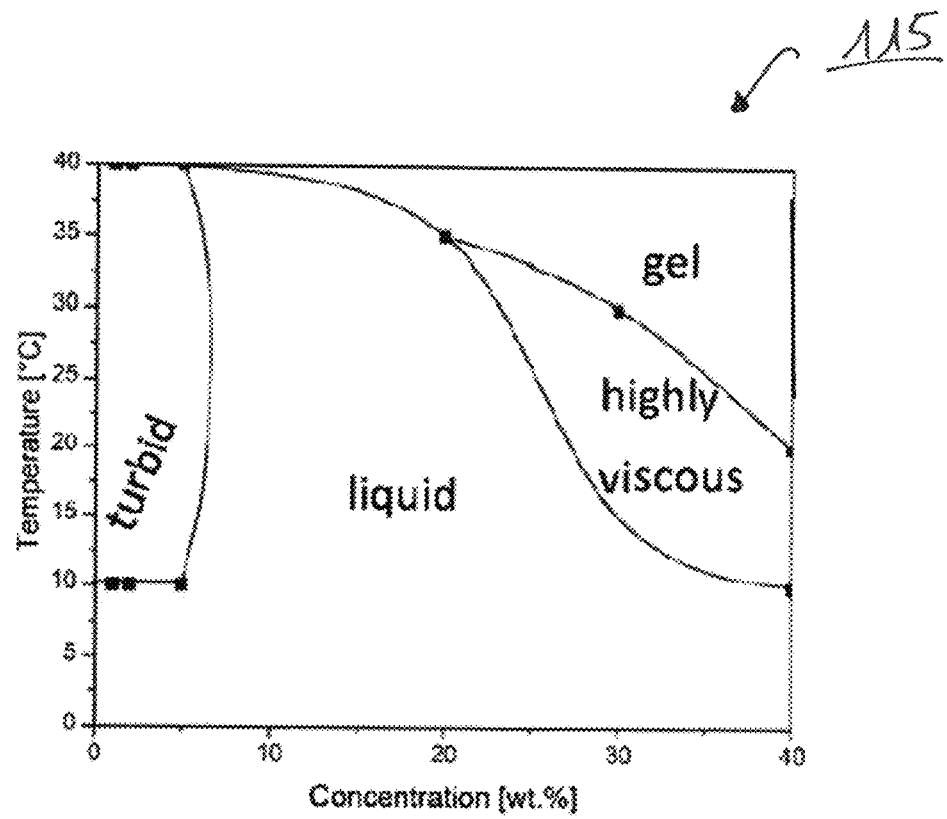
FIG. 21 shows a phase diagram of aqueous solutions of Methyl-P[nPrOzi$_{50}$-b-MeOx$_{50}$]-piperidine-4-carboxylic acid ethyl ester (P2) dependent on concentration and temperature.

Interestingly, at 5 wt.-% (curve 35) (and above LCST of nPrOzi), the solution became turbid (see also Phase diagram 115 in FIG. 21). The viscosity remained very low and decreased monotonously with temperature. In contrast, between approximately 10 and 20 wt.-% (curves 37 and 47) the solutions remained clear and liquid over the whole temperature range investigated (5 to 50° C.). The increase of viscosity started consistently around LCST, while the maximum of the viscosity goes through a plateau that shifts to higher temperatures with increasing polymer concentration.

At concentrations of 20 wt.-% and above, the solutions eventually gel. In this behavior the novel thermogelling polymers are quite distinct from F127 and P123, which also form gels at elevated temperature and/or concentration and are commonly used for gel plotting in biofabrication (N. E. Fedorovich, J. R. de Wijn, A. J. Verbout, J. Alblas, W. J. A. Dhert, *Tissue Eng. Part A* 2008, 14, 127-133). Important for the prospective use as injectable hydrogel or as bioink, the viscosity of the new material at low temperature is relatively low, in particular compared to the viscosity of Pluronic® block copolymers (compare 700 mPa*s (F127) vs. 7 mPa*s (P2) at 10 wt.-% and 10° C.). Even at 30 wt.-%, a solution of P2 at 10° C. (curve 49 in FIG. 11) has a lower viscosity (approx. 50%) than a 10 wt.-% solution of F127 (curve 51 in FIG. 11), which never forms a gel at this concentration. Based on these rheological experiments, it is possible to sketch a preliminary phase diagram for the new thermoresponsive materials.

Figure 12:
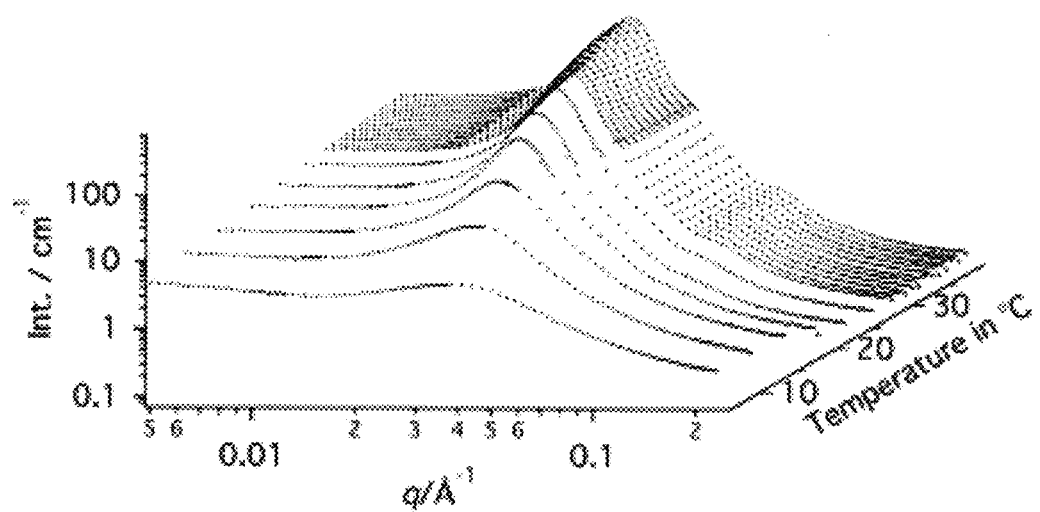
FIG. 12 shows temperature-dependent SANS scattering data of Methyl-P[nPrOzi$_{50}$-b-MeOx$_{50}$]-piperidine-4-carboxylic acid ethyl ester at 20 wt.-%.

This distinct rheological behavior is likely to be linked to the structure of polymer self-assemblies in water. For many, if not most thermogelling polymers the gelation is explained through an aggregation of spherical micelles into a cubic lattice. The novel hydrogel (batch P1, 20 wt.-%) was studied using small angle neutron scattering (SANS) at different temperatures (FIG. 12).

Instead, a model of a bi-continuous sponge-like structure as described by Teubner et al. was tested (M. Teubner, R. Strey, *J. Chem. Phys.* 1987, 87, 3195-3200). The expression they found is $$I(q) = \frac{C}{a_2 + c_1 q^2 + c_2 q^4}$$

Figure 13:
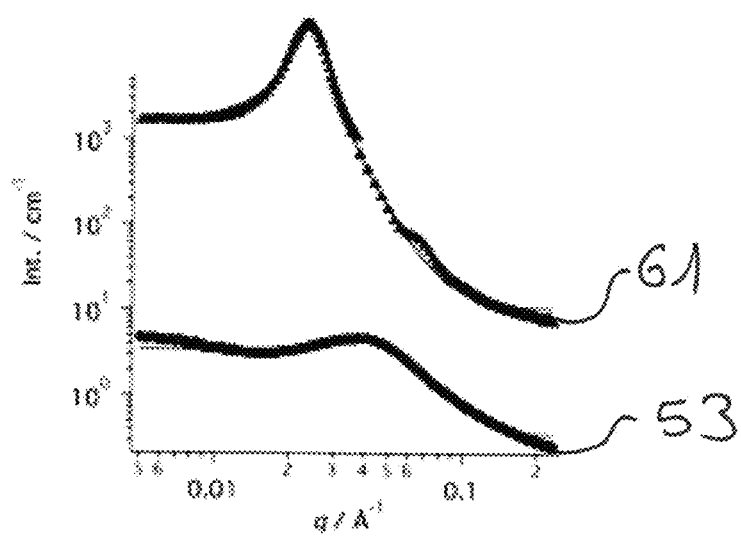
FIG. 13 shows representative fits for a bi-continuous sponge like structure for lowest temperature (at 6.9° C.) and highest temperature (39.7° C.) of Methyl-P[nPrOzi$_{50}$-b-MeOx$_{50}$]-piperidine-4-carboxylic acid ethyl ester at 20 wt.-%.

Here the proportionality constant C=(8π)/ξ⟨η²⟩c$_2$V with ⟨η²⟩ being the mean square fluctuation of the scattering density p and f is the correlation length c$_1$ and c$_2$ are given by $$\xi = \left[\frac{1}{2}\left(\frac{a_2}{c_2}\right)^{1/2} + \frac{1}{4}\frac{c_1}{c_2}\right]^{-1/2}$$

and $$d = 2\pi\left[\frac{1}{2}\left(\frac{a_2}{c_2}\right)^{1/2} - \frac{1}{4}\frac{c_1}{c_2}\right]^{-1/2}$$

wherein d is the characteristic domain size (periodicity). Ti model allows to fit the SANS data very well and yielded characteristic domain sizes and correlation lengths between 50 and 350 Å, depending on the temperature. This can be seen in FIG. 13, which shows the representative fits for a bi-continuous sponge-like structure for lowest temperature at 6.9° C. (curve 53) and highest temperature 39.7° C. (curve 61). For better visibility, the SANS scattering data at 39.7° C. (curve 61) and its respective fit was y-shifted using a factor of 64.

Figure 14:
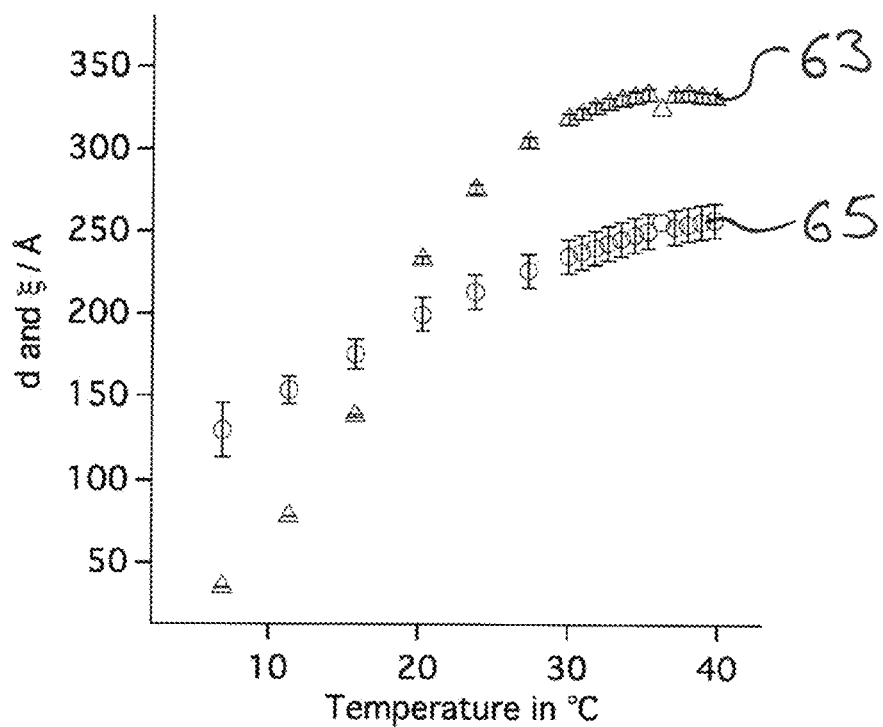
FIG. 14 shows resulting correlation length ξ and characteristic domain size d of Methyl-P[nPrOzi$_{50}$-b-MeOx$_{50}$]-piperidine-4-carboxylic acid ethyl ester at 20 wt.-%.

FIG. 14 shows the resulting correlation length ξ (curve 63) and characteristic domain size d (curve 65) of Methyl-P[nPrOzi$_{50}$-b-MeOx$_{50}$]-piperidine-4-carboxylic acid ethyl ester. Important to note, the correlation length is a cutoff length, above which correlations are no longer noticeable in the system. As temperature increases, an increase in the domain size as well as in the correlation length was observed, the latter eventually exceeding the former (at approximately 18° C.).

As this is well below the gelation temperature, the correlation length apparently needs to exceed the characteristic distance considerably for a macroscopic rheological response from the system to occur. At temperatures just below 30° C., the increase of the correlation length levels off, which coincides with macroscopic gelation observed at ≈27° C. Both, SANS and rheology confirm that the structure of the novel hydrogels is very distinct from the commonly used Pluronic gels. This may open up new avenues for their use as biomaterials.

Figure 15:
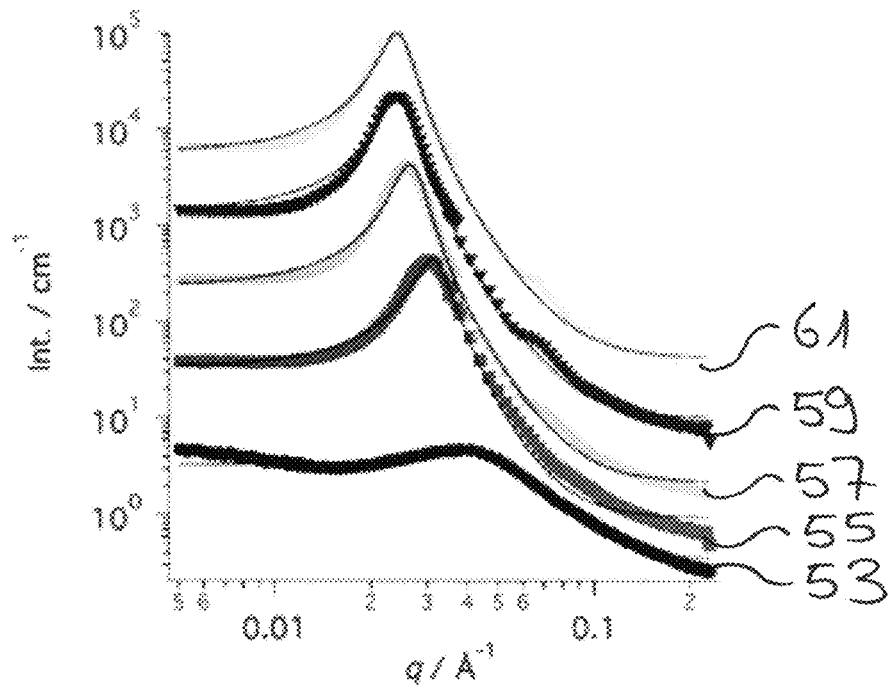
FIG. 15 shows fits of selected datasets over the complete temperature range of Methyl-P[nPrOzi$_{50}$-b-MeOx$_{50}$]-piperidine-4-carboxylic acid ethyl ester at 20 wt.-%.

FIG. 15 shows the representative fits for a bi-continuous sponge like structure of selected datasets over the complete temperature range of Methyl-P[nPrOzi$_{50}$-b-MeOx$_{50}$]-piperidine-4-carboxylic acid ethyl ester. For better visibility, SANS scattering data and their respective fits were shifted using a factor of 1 (6.9° C., curve 53), a factor of 4 (21.1° C., curve 55), a factor of 16 (30.0° C., curve 57), a factor of 64 (36.2° C., curve 59) and a factor of 256 (39.7° C., curve 61), respectively.

Figure 16:
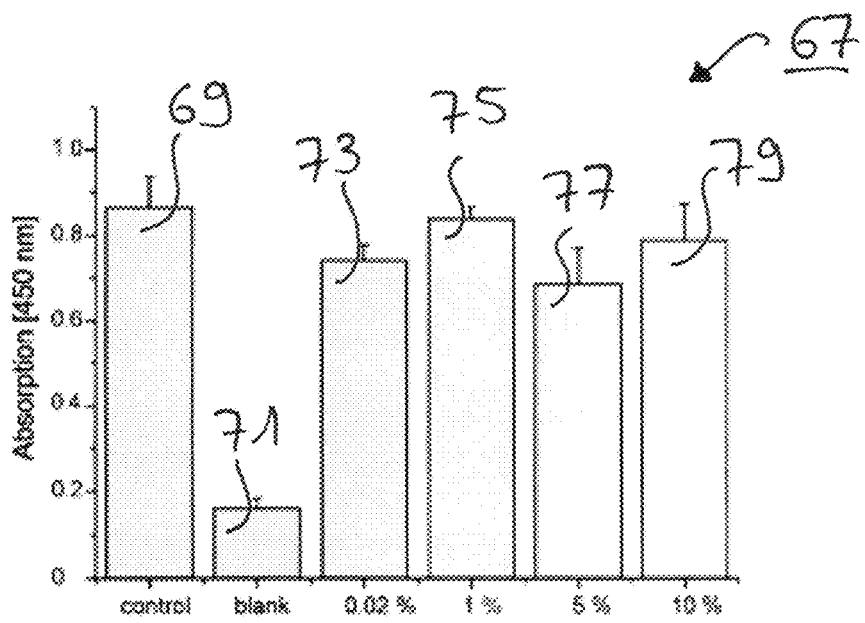
FIG. 16 shows the proliferation of NIH-3T3 cells in the presence of various polymer concentrations of Methyl-P[nPrOzi$_{50}$-b-MeOx$_{50}$]-piperidine-4-carboxylic acid ethyl ester as analyzed by WST-1 assay at 20 wt.-%.

At non-gelling concentrations of up to 100 g/L no marked dose-dependent cytotoxicity in murine NIH 3T3 fibroblasts were found. The results can be taken out of bar chart 67 in FIG. 16 (bar 69: control sample, bar 71: blank sample, bar 73: 0.02 wt.-%, bar 75: 1 wt.-%, bar 77: 5 wt.-% and bar 79: 10 wt.-%). This is remarkable, as Schubert and co-workers found cytotoxicity below this concentration for POx homopolymers (M. Bauer, S. Schroeder, L. Tauhardt, K. Kempe, U. S. Schubert, D. Fischer, *J. Polym. Sci., Part A: Polym. Chem.* 2013, 51, 1816-1821.; M. Bauer, C. Lautenschlaeger, K. Kempe, L. Tauhardt, U. S. Schubert, D. Fischer, *Macromol. Biosci.* 2012, 12, 986-998).

At even higher concentration, the polymer undergoes gelation below 37° C., also in cell culture media. Therefore, cells were suspended in cell culture media supplemented with 25 wt.-% P2 and incubated for 24 h at 37° C. Also under these condition, the polymers/gels exhibited very good cytocompatibility. The results can be seen in FIGS. 17 to 19.

Figure 17:
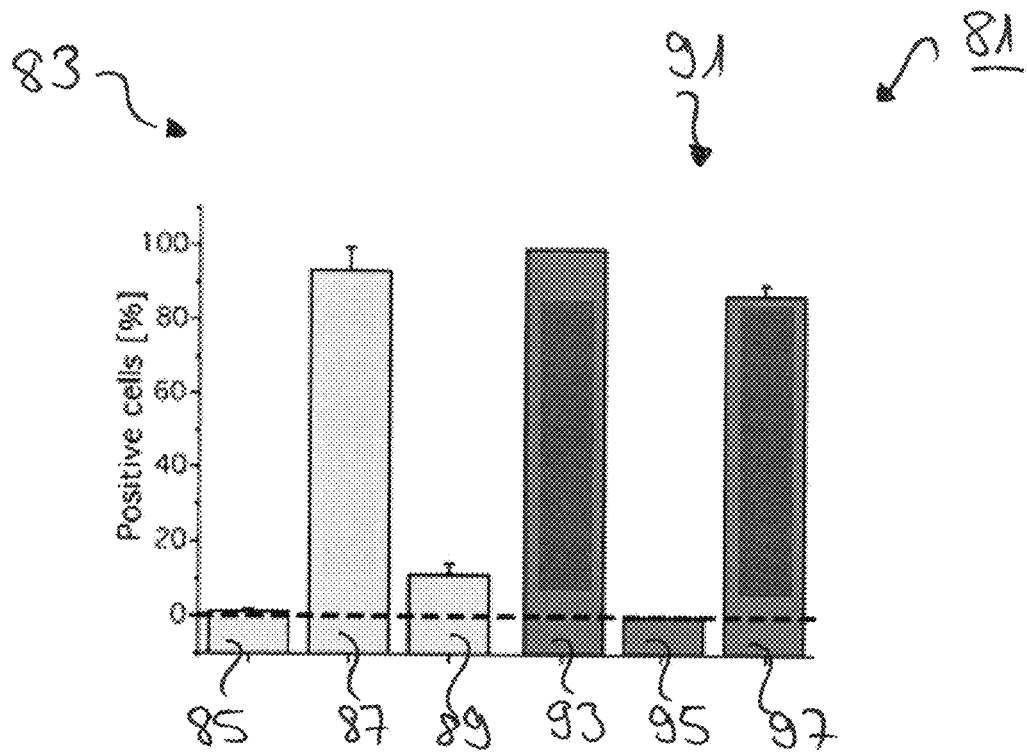
FIG. 17 shows Cell viability of NIH 3T3 fibroblasts.

FIG. 17 shows the cell viability of NIH 3T3 fibroblasts as a bar chart 81. The bar chart 81 shows results for PI staining 83 with a bar 85 for the control sample, a bar 87 for the methanol treated sample and a bar 89 for the sample with cells in 25% of gel. As well, the bar chart 81 shows results for FDA staining 91 with a bar 93 for the control sample, a bar 95 for the methanol treated sample and a bar 97 for the sample with cells in 25% of gel.

Figure 18:
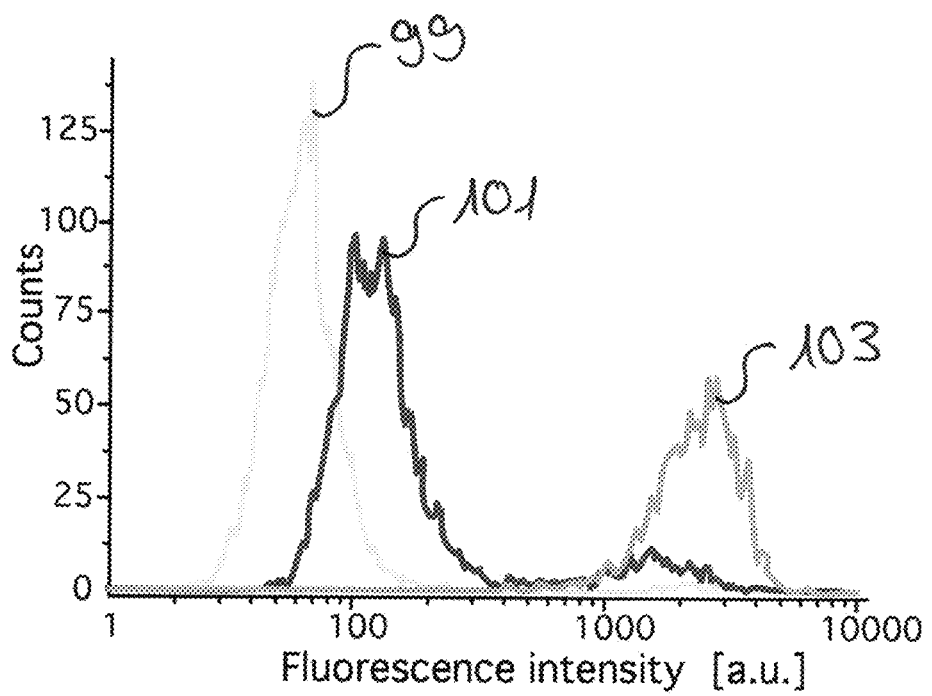
FIG. 18 shows a flow cytometry analysis of Methyl-P[nPrOzi$_{50}$-b-MeOx$_{50}$]-piperidine-4-carboxylic acid ethyl ester at 20 wt.-%.

FIG. 18 shows a flow cytometry analysis (FACS Calibur system) of NIH 3T3 fibroblasts cultivated in Methyl-P[nPrOzi$_{50}$-b-MeOx$_{50}$]-piperidine-4-carboxylic acid ethyl ester, using a 488 nm laser with the emission channel FL2 (585 nm/±21 nm) for PI staining 83 (compare to FIG. 17) with curve 99 for control sample (see bar 85 in FIG. 17), curve 103 for the methanol treated sample (see bar 87 in FIG. 17) and curve 101 for the sample with cells in 25% of gel (see bar 89 in FIG. 17). A total number of 5000 events were counted with BD CellQuest™ Pro and the geometric mean fluorescence intensity was determined for each condition using Flowing Software (version 2.5.1; Turku Bioimaging).

Figure 19:
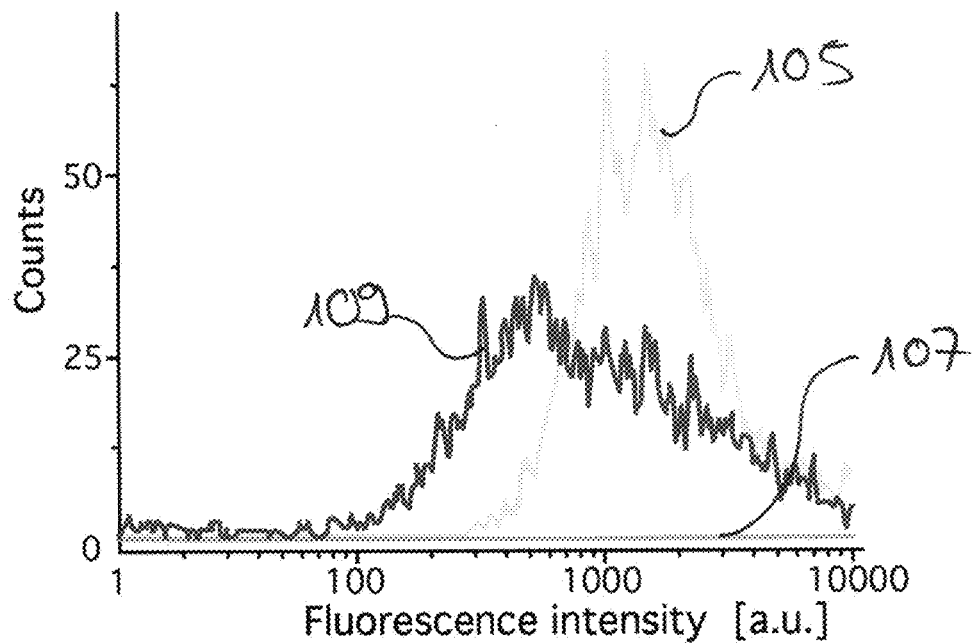
FIG. 19 shows a flow cytometry analysis of NIH 3T3 fibroblasts cultivated in Methyl-P[nPrOzi$_{50}$-b-MeOx$_{50}$]-piperidine-4-carboxylic acid ethyl ester at 20 wt.-%.

FIG. 19 shows a flow cytometry analysis of NIH 3T3 fibroblasts cultivated in Methyl-P[nPrOzi$_{50}$-b-MeOx$_{50}$]-piperidine-4-carboxylic acid ethyl ester for the emission channel FL1 (530 nm/±15 nm) for FDA staining 91 (compare to FIG. 17) with curve 105 for control sample (see bar 93 in FIG. 17), curve 107 for the methanol treated sample (see bar 95 in FIG. 17) and curve 109 for the sample with cells in 25% of gel (see bar 97 in FIG. 17).

Figure 20:
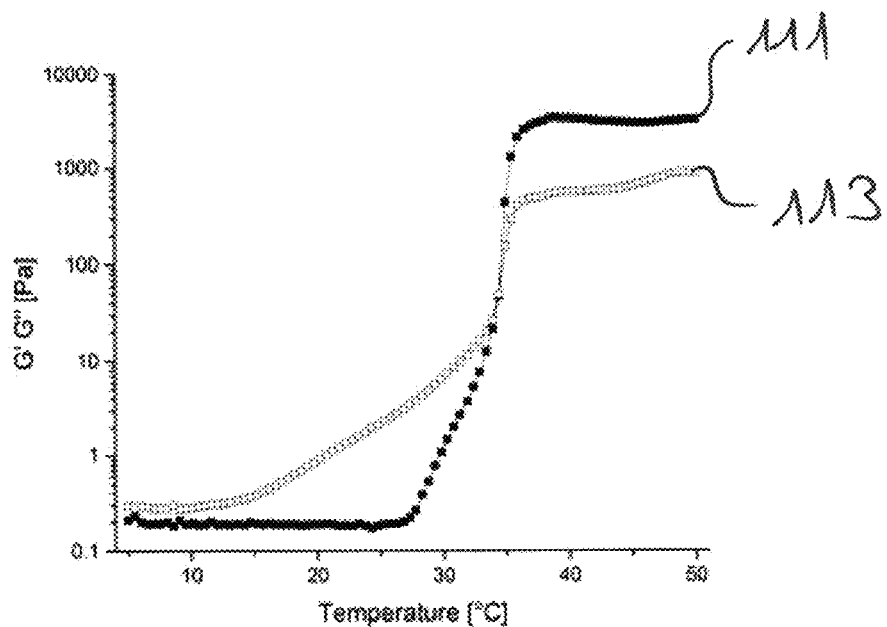
FIG. 20 shows a temperature-dependent rheological analysis of Methyl-P[nPrOzi$_{50}$-b-MeOx$_{50}$]-piperidine-4-carboxylic acid ethyl ester (P2) at a concentration of 20 wt.-%.

In FIG. 20 a temperature-dependent rheological analysis of Methyl-P[nPrOzi$_{50}$-b-MeOx$_{50}$]-piperidine-4-carboxylic acid ethyl ester at a concentration of 20 wt.-% (batch P2) is shown. Curve 111 shows the temperature-dependence of the storage modulus (G'), curve 113 shows the temperature-dependence of the loss modulus (G"). The gel point, determined at the intersection of G' and G", is located at 35° C., so just below body temperature. The gel point moves to lower temperatures with increasing the molar mass. The resulting hydrogels are quite soft with a loss modulus (G') of around 4 kPa. In contrast to the gelling temperature, the storage modulus (G') seems to be independent of the molar mass.

FIG. 21 shows a phase diagram 115 of aqueous solutions of Methyl-P[nPrOzi$_{50}$-b-MeOx$_{50}$]-piperidine-4-carboxylic acid ethyl ester dependent on concentration and temperature. Increasing temperature, at concentrations below 10 wt.-% muddy solutions are obtained, which can be explained by nano- and microscaling aggregation.

Further, several batches (P1a to P6a) of R—P[nPrOzi$_{100}$-b-MeOx$_{100}$]-R$^1$ were analyzed using gel permeation chromatography (GPC) (FIGS. 24 and 25), temperature dependent rheological properties (FIGS. 22, 23 and 31) and $^1$H-NMR spectra (FIGS. 26 to 30 and 32). The results are first summarized in following Table 2.

TABLE 2

Degree of Polymerization (DP) and molar masses (kg/mol) obtained by NMR and GPC of batches P1a to P6a.

| | DP $_{theo.}$ | DP$_{exp}$[a] | M$_n$ $_{theo.}$ | M$_n$ | Mw | Đ |
|---|---|---|---|---|---|---|
| P1a | 99/100 | 94/94 | 21.3 | 7.0[c] | 9.4[c] | 1.34[c] |
| P2a | 102/104 | 110/104 | 22.0 | 8.1[c] | 11.5[c] | 1.42[c] |
| P3a | 100/100 | 100/99 | 21.4 | 12.3[b] | 19.2[b] | 1.56[b] |
| P4a | 100/100 | 100/97 | 21.4 | 14.7[b] | 21.2[b] | 1.44[b] |
| P5a | 100/100 | 99/95 | 21.3 | 15.9[b] | 20.8[b] | 1.31[b] |
| P6a | 50/45/5 | 55/50/6 | 10.9 | 6.4[c] | 7.4[c] | 1.15[c] |

[a]Determined by end-group analysis ($^1$H NMR spectroscopy in MeOD-d$^4$ (300 MHz, 298 K));
[b]Determined from GPC in DMF with LiBr (1 g/L) at 313 K;
[c]Determined form GPC in HFIP with potassium triflate (3 g/L) at 313 K.

Figure 22:
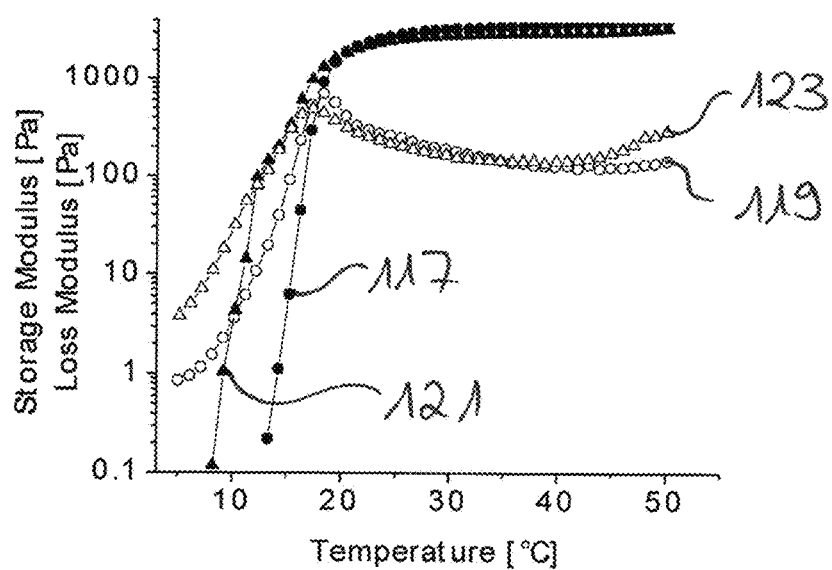
FIG. 22 shows the temperature dependent rheology with storage modulus (G') and loss modulus (G") for 20 wt.-% of Methyl-P[nPrOzi$_{100}$-b-MeOx$_{100}$]-piperidine-4-carboxylic acid ethyl ester and Methyl-P[nPrOzi$_{100}$-b-MeOx$_{100}$]-tert-butyl-piperazine-1-carboxylat.

FIG. 22 shows the temperature dependent rheology with storage modulus (G') and loss modulus (G") for 20 wt.-% of Methyl-P[nPrOzi$_{100}$-b-MeOx$_{100}$]-piperidine-4-carboxylic acid ethyl ester (batch P1a) and Methyl-P[nPrOzi$_{100}$-b-MeOx$_{100}$]-tert-butyl-piperazine-1-carboxylate (batch P2a). Storage modulus (G') and loss modulus (G") of batch P1a are represented by curves 117, 119 and storage modulus (G') and loss modulus (G") of batch P2a are represented by curves 121, 123. It can be seen, that the use of 1-BOC Piperazine (curves 121, 123) instead of ethyl-4-piperidinecarboxylate (curves 117, 119) as a termination molecule does no influence the gelation behavior of the block copolymer. The storage modulus G' as well as loss modulus (G") remain unchanged.

Figure 23:
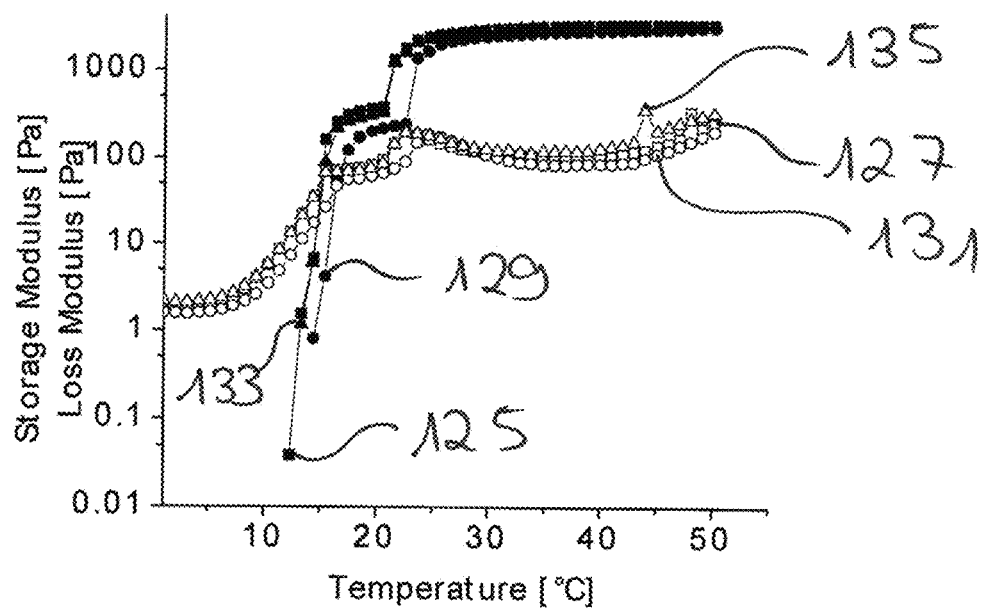
FIG. 23 shows the temperature dependent rheology with storage modulus (G') and loss modulus (G") for 20 wt.-% of Propynyl-P[nPrOzi$_{100}$-b-MeOx$_{100}$]-piperidine-4-carboxylic acid ethyl ester, Propynyl-P[nPrOzi$_{100}$-b-MeOx$_{10}$]-methyl 3-mercaptopropionate and Propynyl-P[nPrOzi$_{100}$-b-MeOx$_{100}$]-hydroxy.

Same can be taken out of FIG. 23. FIG. 23 shows the temperature dependent rheology with storage modulus (G') and loss modulus (G") for 20 wt.-% of Propynyl-P[nPrOzi$_{100}$-b-MeOx$_{100}$]-piperidine-4-carboxylic acid ethyl ester (batch P3a), Propynyl-P[nPrOzi$_{100}$-b-MeOx$_{100}$]-methyl 3-mercaptopropionate (batch 4a) and Propynyl-P[nPrOzi$_{100}$-b-MeOx$_{100}$]-hydroxy (batch 5a). Storage modulus (G') and loss modulus (G") of batch P3a are represented by curves 125, 127, storage modulus (G') and loss modulus (G") of batch P4a are represented by curves 129, 131 and storage modulus (G') and loss modulus (G") of batch P5a are represented by curves 133, 135.

The results shown in FIG. 23 also suggest, that the observed effects occur independently of the end groups. By using different N-, O- and S-nucleophiles as termination molecules, the results shown in FIG. 22 could be verified showing the broad range of possible termination molecules used for synthesis.

Figure 24:
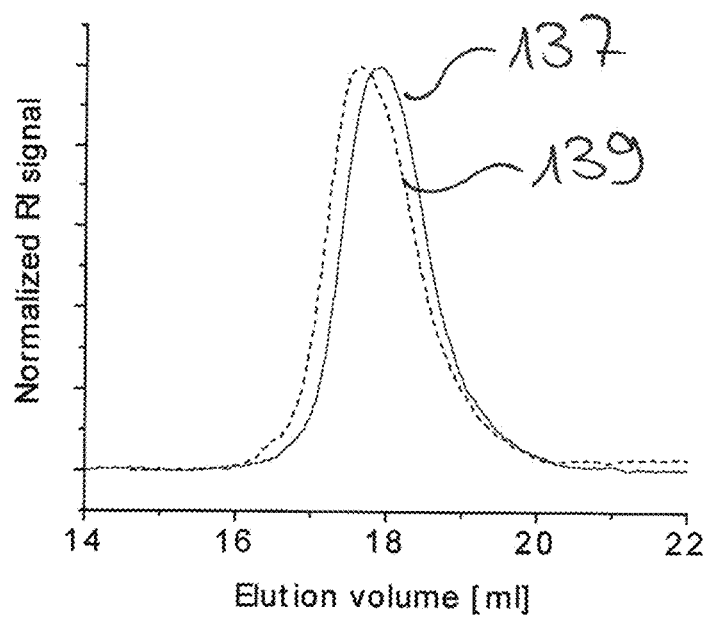
FIG. 24 shows GPC traces of Methyl-P[nPrOzi$_{100}$-b-MeOx$_{100}$]-piperidine-4-carboxylic acid ethyl ester and Methyl-P[nPrOzi$_{100}$-b-MeOx$_{100}$]-tert-butyl-piperazine-1-carboxylat.

FIG. 24 shows the GPC traces of batch P1a (curve 137) and batch P2a (curve 139) measured in HFIP. The GPC elugrammes 137, 139 have a moderately narrow molecular weight distribution ((Ð<1.5) and also show no differences as a result of the used termination molecule.

Figure 25:
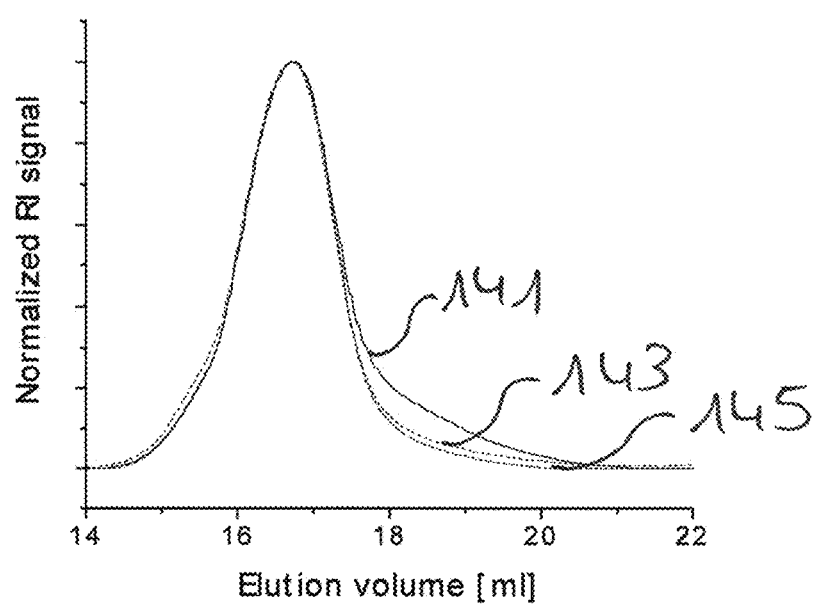
FIG. 25 shows GPC traces of Propynyl-P[nPrOzi$_{100}$-b-MeOx$_{100}$]-piperidine-4-carboxylic acid ethyl ester, Propynyl-P[nPrOzi$_{100}$-b-MeOx$_{100}$]-methyl 3-mercaptopropionate and Propynyl-P[nPrOzi$_{100}$-b-MeOx$_{100}$]-hydroxy.
Figure 26:
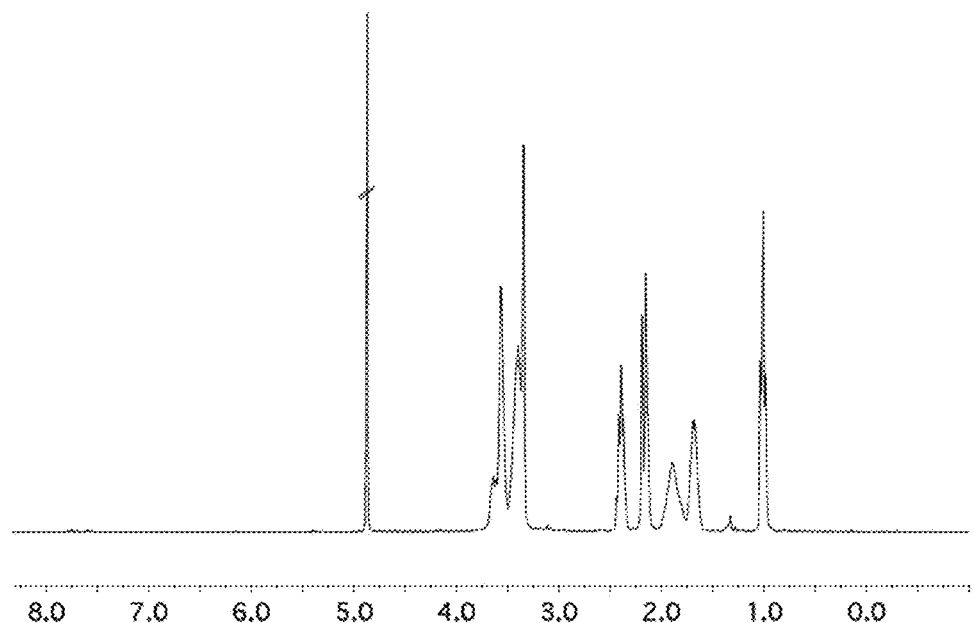
FIG. 26 shows an $^1$H-NMR spectra of Methyl-P[nPrOzi$_{100}$-b-MeOx$_{100}$]-piperidine-4-carboxylic acid ethyl ester in methanol-d$^4$ at 298 K.
Figure 27:
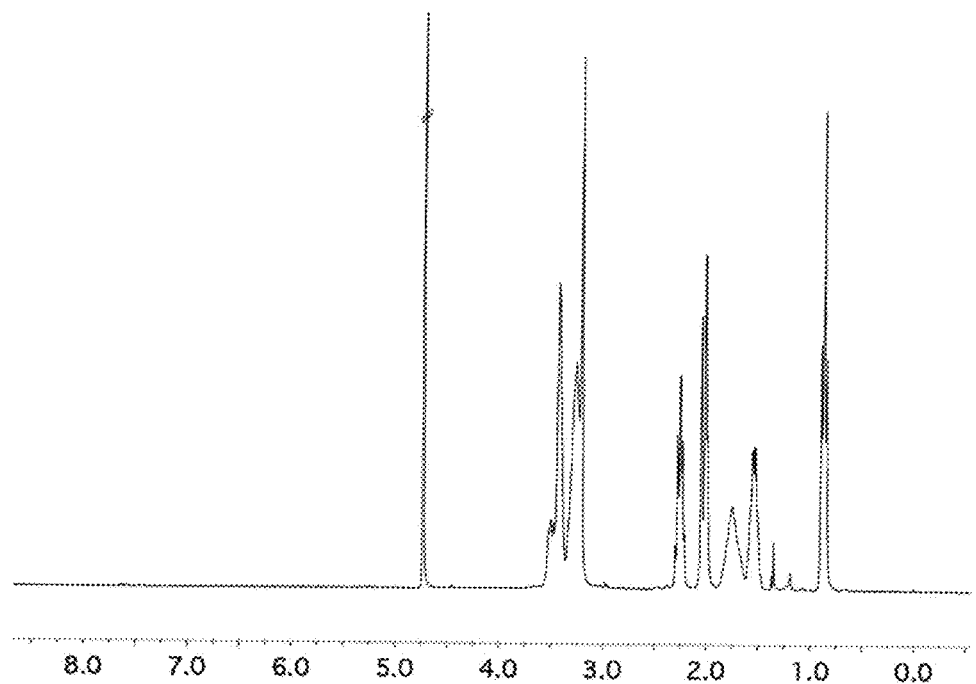
FIG. 27 shows an $^1$H-NMR spectra of Methyl-P[nPrOzi$_{100}$-b-MeOx$_{100}$]-tert-butyl-piperazine-1-carboxylat in methanol-d$^4$ at 298 K.
Figure 28:
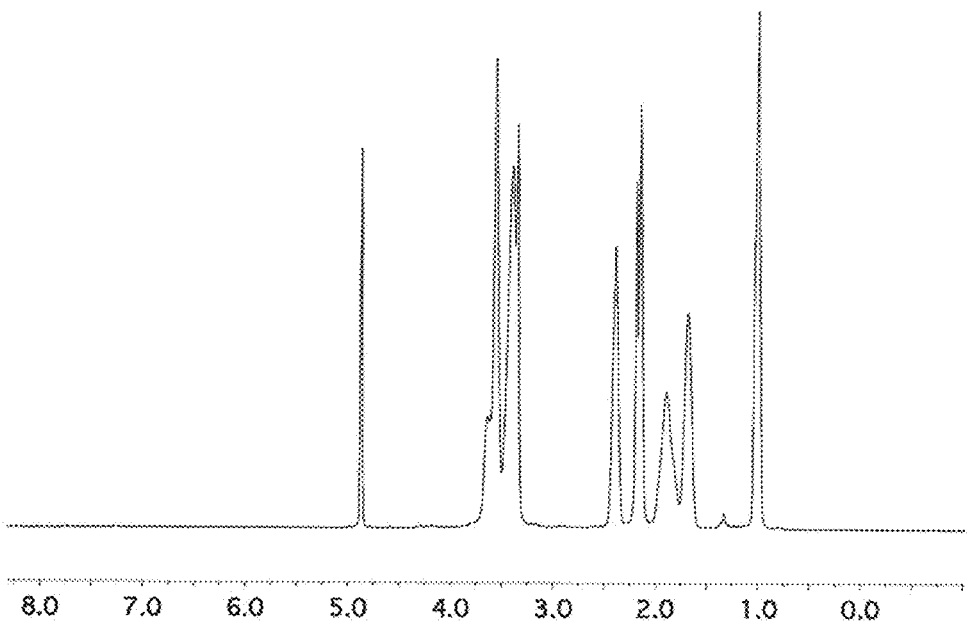
FIG. 28 shows an $^1$H-NMR spectra of Propynyl-P[nPrOzi$_{100}$-b-MeOx$_{100}$]-piperidine-4-carboxylic acid ethyl ester in methanol-d$^4$ at 298 K.
Figure 29:
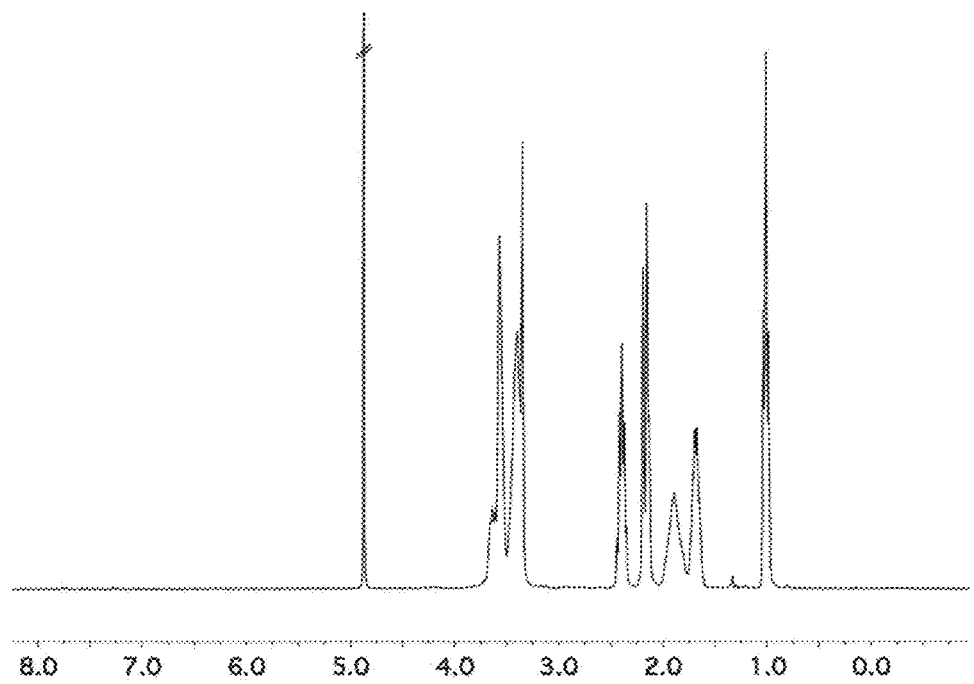
FIG. 29 shows an 1H-NMR spectra of Propynyl-P[nPrOzi$_{100}$-b-MeOx$_1$]-methyl 3-mercaptopropionate in methanol-d$^4$ at 298 K.
Figure 30:
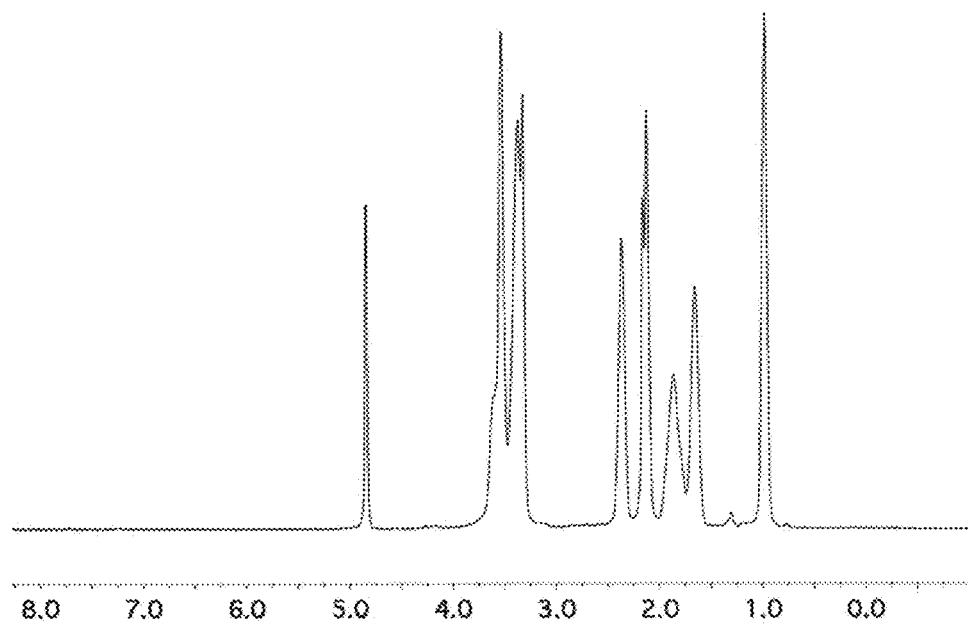
FIG. 30 shows an 1H-NMR spectra of Propynyl-P[nPrOzi$_{100}$-b-MeOx$_{10}$]-hydroxy in methanol-d$^4$ at 298 K.

FIG. 25 shows the GPC traces of batch P3a (curve 141), batch P4a (curve 143) and batch P5a (curve 145) measured in DMF. These polymers were used for the preparation of the gels, which are characterized by the temperature-sweep shown in FIG. 23.

FIGS. 26 to 30 show the 1H-NMR spectra of batches P1a (FIG. 26), P2a (FIG. 27), P3a (FIG. 28), P4a (FIG. 29) and P5a (FIG. 30) in methanol-d$^4$ at 298 K each. The 1H-NMR spectra 26, 27, 28, 29, 30 of all block copolymers show that there are no detectable rests of solvent, which may influence the gelling process (the formation of the gel) of the respective block copolymer. In addition, the desired degree of polymerization could be determined by endgroup analysis.

Figure 31:
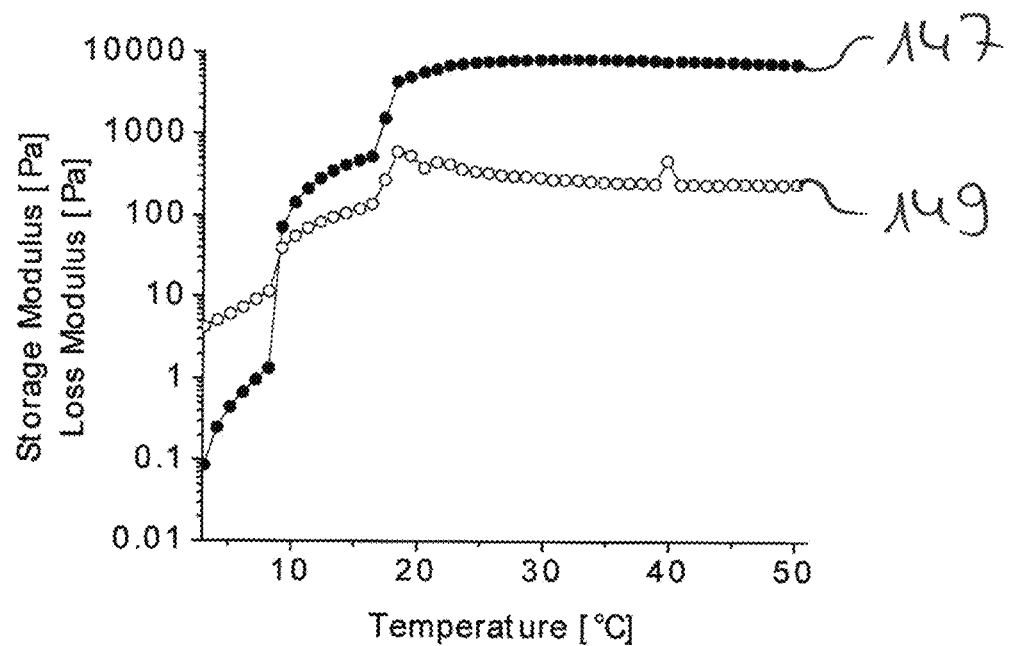
FIG. 31 shows the temperature dependent rheology with storage modulus (G') and loss modulus (G") for 20 wt.-% of Methyl-P[nPrOzi$_{50}$-b-MeOx$_{50}$]-tert-butyl-piperazine-1-carboxylat, contaminated with 10% Poly(n-butyl-2-oxazin)
Figure 32:
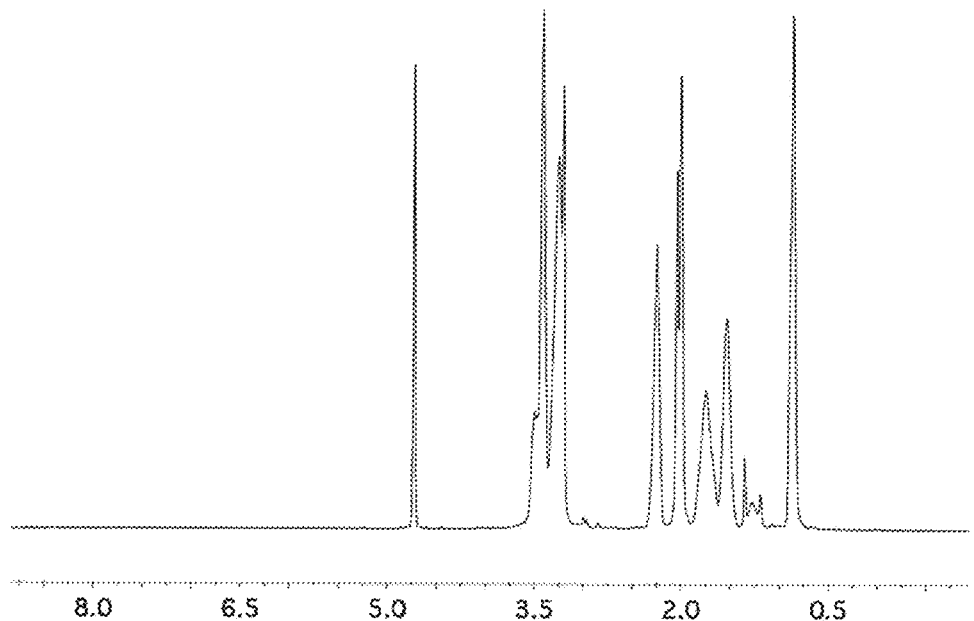
FIG. 32 shows an $^1$H-NMR spectra of Methyl-P[nPrOzi$_{50}$-b-MeOx$_{50}$]-tert-butyl-piperazine-1-carboxylat, contaminated with 10% Poly(n-butyl-2-oxazin)

FIG. 31 shows the temperature dependent rheology with storage modulus (G') and loss modulus (G") for 20 wt.-% of contaminated Methyl-P[nPrOzi$_{50}$-b-MeOx$_{50}$]-tert-butyl-piperazine-1-carboxylat (batch P6a). The storage modulus (G') is represented by curve 147 and the loss modulus (G") is represented by curve 149. FIG. 32 shows an $^1$H-NMR spectra of batch P6a.

In detail, the Poly(2-n-propyl-2-oxazin)-block was deliberately contaminated with 10% Poly(n-butyl-2-oxazin). The resulting block copolymers are opaque, but exhibit storage modulus (G') that is increased by a factor of 2 (curve 147). As a result, the material can store more deformation energy and influences the effect of reverse deformation. Due to the more pronounced elastic character, a higher degree of crosslinking can be assumed. In this context, it must be taken into account, that it is exclusively a reversible physical crosslinking reaction.

Figure 33:
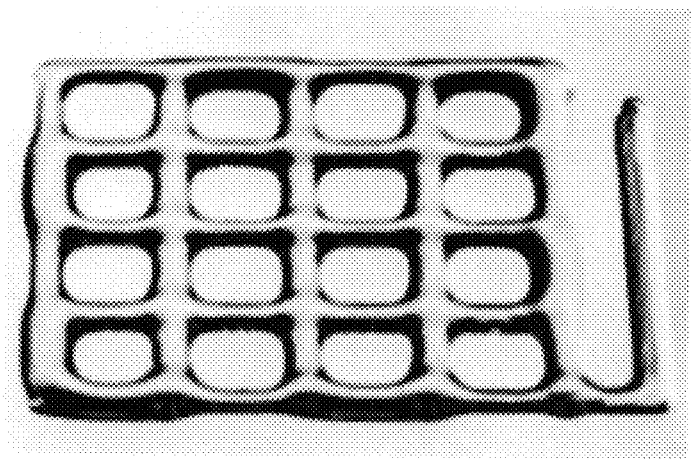
FIG. 33 shows a light microscope image of a printed constructs composed of orthogonal stacks of hydrogel strands with a base area of 12×12 mm$^2$ and a strand-center to strand-center distance of 3 mm.

FIG. 33 shows a light microscope image of a printed constructs composed of orthogonal stacks of hydrogel strands. To be able to work at room temperature without risking ink liquefaction, experiments were conducted using a 20 wt.-% concentration of batch P2a. The pronounced shear thinning of the material enabled processing it at room temperature with a pressure of 1.2 bars using 0.25 mm inner diameter needles. With these settings, it was possible to generate defined constructs composed of orthogonal stacks of hydrogel strands with a base area of 12×12 mm$^2$ and a strand-center to strand-center distance of 3 mm.

Figure 34:
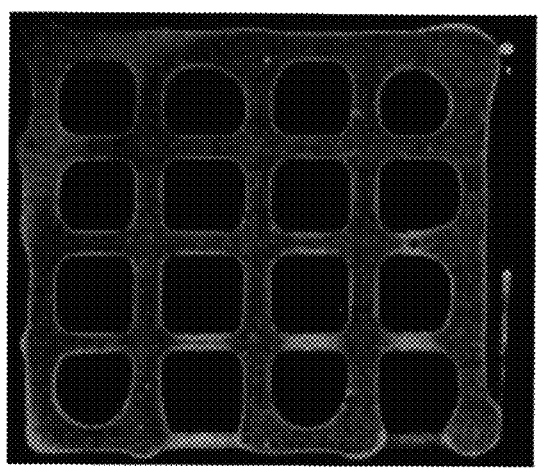
FIG. 34 shows cell loaded constructs.

Furthermore, as can be seen in FIG. 34, by mixing 1.0 million NIH-3T3 fibroblasts into this ink cell loaded constructs could be generated. The cells did not influence the printability of the material and the same setting as for cell-free inks could be applied to process the bioinks.

The cell distribution within the constructs was homogeneous throughout the entire constructs. The homogenous cell distribution was facilitated due to the thermoresponsive properties of the material. At low temperatures (ice bath) the ink has a very low viscosity and cells are readily distributed within the material via repeated mixing by pipetting. Once taken of the ice, the immediate, temperature driven viscosity increase preserved the homogenous cell distribution within the ink until the material was dispensed. As noted by Malda et al., it can be challenging to homogeneously distribute cells in highly viscous bioinks due to various issues (air bubbles, difficult pipetting/handling) (V. H. M. Mouser, F. P. W. Melchels, J. Visser, W. J. A. Dhert, D. Gawlitta, J. Malda, *Biofabrication* 2016, 8, 35003).

Figure 35:
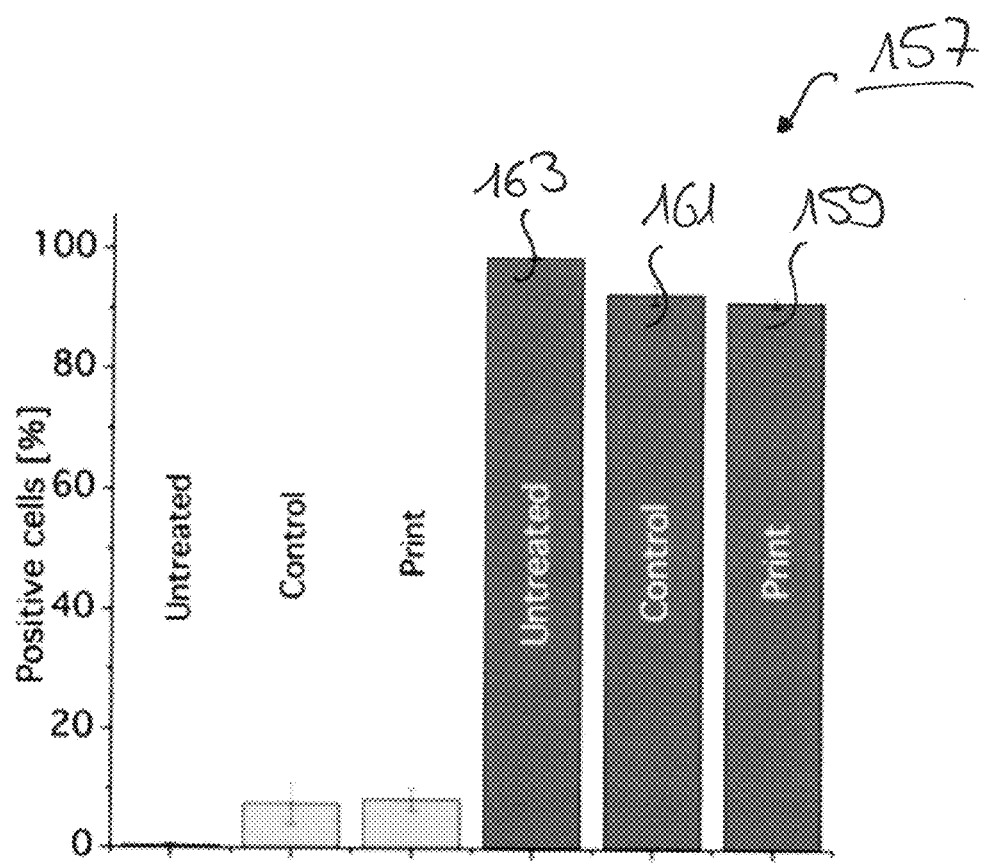
FIG. 35 shows results of FACS analysis on the influence of the printing process on the viability of NIH 3T3 fibroblasts.

To analyze if dispensing had a negative effect on cell viability, NIH-3T3 cells included into biofabricated scaffolds were further investigated via flow cytometry. The results can be taken out of FIG. 35. While the untreated control represents cells in medium, the control represents cells that were dispersed in the bioink but not printed. This revealed similar levels of cytocompatibility (91.5%±0.8%—bar 159) compared to cells incorporated into the material without further processing (92.8%±1.7%—bar 161) and untreated control cells (98.9%±0.18%—bar 163) Therefore, the printing process seems to have no effect on the cell viability when using our bioink.

In summary, new thermogelling synthetic block copolymers are presented, comprising a hydrophilic block [A] or [B] and a thermoresponsive block [A] or [B], which are an excellent bioink candidates. The new gels are optical transparent and have a very suitable and adjustable gelling temperature. The synthesis of the polymers is easy and to be scaled well. The gelation process of all describes molecules is very fast. The combination of thermogelation, excellent biocompatibility and isothermal shear-thinning is particularly attractive for many applications including drug delivery, biofabrication, cell culture or tissue engineering. The particularities of the rheological properties can be conveniently fine-tuned via the polymer composition while the chemical functionalization via chain termini can be realized without having an impeding influence on the desirable rheological properties.

The following is a summary list of reference numerals and the corresponding structure used in the above description of the invention:

1 GPC trace of batch P1 (Methyl-P[nPrOzi$_{50}$-b-MeOx$_{50}$]-piperidine-4-carboxylic acid ethyl ester)
3 GPC trace of batch P2 (Methyl-P[nPrOzi$_{50}$-b-MeOx$_{50}$]-piperidine-4-carboxylic acid ethyl ester)
5 GPC trace of batch P3 (Methyl-P[nPrOzi$_{50}$-b-MeOx$_{50}$]-piperidine-4-carboxylic acid ethyl ester)
7 GPC trace of batch P4 (Methyl-P[nPrOzi$_{50}$-b-MeOx$_{50}$]-piperidine-4-carboxylic acid ethyl ester)
9 GPC trace of batch P5 (Methyl-P[nPrOzi$_{50}$-b-MeOx$_{50}$]-piperidine-4-carboxylic acid ethyl ester)
11 Storage modulus (G') of batch P1
13 Storage modulus (G') of batch P2
15 Storage modulus (G') of batch P3
17 Storage modulus (G') of batch P4
19 Storage modulus (G') of batch P5
21 Loss modulus (G") of batch P1
22 Loss modulus (G") of batch P2
23 Loss modulus (G") of batch P3
24 Loss modulus (G") of batch P4
25 Loss modulus (G") of batch P5
26 Loss modulus (G') at 10° C. and 10 rad/s for batch P2
27 Storage modulus (G') at 10° C. and 10 rad/s for batch P2
28 Storage modulus (G') at 50° C. and 10 rad/s for batch P2
29 Loss modulus (G') at 50° C. and 10 rad/s for batch P2
31 Flow curve for batch P2
33 Storage modulus (G') of batch P2
34 Loss modulus (G") of batch P2
35 Dynamic viscosity of batch P2 (5 wt.-%)

37 Dynamic viscosity of batch P2 (10 wt.-%)
41 Dynamic viscosity of batch P2 (12.5 wt.-%)
43 Dynamic viscosity of batch P2 (15 wt.-%)
45 Dynamic viscosity of batch P2 (17.5 wt.-%)
47 Dynamic viscosity of batch P2 (20 wt.-%)
49 Dynamic viscosity of batch P2 (30 wt.-%)
51 comparison curve for F127 (10 wt.-%)
53 SANS Scattering data for batch P2 (6.9° C.)
55 SANS Scattering data for batch P2 (21.1° C.)
57 SANS Scattering data for batch P2 (30.0° C.)
59 SANS Scattering data for batch P2 (36.2° C.)
61 SANS Scattering data for batch P2 (39.7° C.)
63 correlation length for batch P2
65 characteristic domain size d for batch P2
67 bar chart dose-dependent cytotoxicity
69 bar control sample
71 bar blank sample
73 bar sample with 0.02 wt.-%
75 bar sample with 1 wt.-%
77 bar sample with 5 wt.-%
79 bar sample with 10 wt.-%
81 bar chart cell viability of NIH 3T3 fibroblasts
83 PI staining bars
85 bar control sample
87 bar methanol treated sample
89 bar of cells in 25% of gel
91 FDA staining bars
93 bar control sample
95 bar methanol treated sample
97 bar of cells in 25% of gel
99 curve control sample (for PI staining)
101 curve of cells in 25% of gel (for PI staining)
103 curve methanol treated sample (for PI staining)
105 curve control sample (for FDA staining)
107 curve methanol treated sample (for FDA staining)
109 curve of cells in 25% of gel (for FDA staining)
111 temperature dependence of storage modulus G' for batch P2
113 temperature dependence of loss modulus G' for batch P2
115 phase diagram of batch P2
117 Storage modulus (G') of batch P1a (Methyl-P[nPrOzi$_{100}$-b-MeOx$_{100}$]-piperidine-4-carboxylic acid ethyl ester)
119 Loss modulus (G") of batch P1a
121 Storage modulus (G') of batch P2a (Methyl-P[nPrOzi$_{100}$-b-MeOx$_{100}$]-tert-butyl-piperazine-1-carboxylat
123 Loss modulus (G''') of batch P2a
125 Storage modulus (G') of batch P3a (Propynyl-P[nPrOzi$_{100}$-b-MeOx$_{100}$]-piperidine-4-carboxylic acid ethyl ester)
127 Loss modulus (G''') of batch P3a
129 Storage modulus (G') of batch P4a (Propynyl-P[nPrOzi$_{100}$-b-MeOx$_{100}$]-methyl 3-mercaptopropionate)
131 Loss modulus (G''') of batch P4a
133 Storage modulus (G') of batch P5a (Propynyl-P[nPrOzi$_{100}$-b-MeOx$_{100}$]-hydroxy)
135 Loss modulus (G''') of batch P5a
137 GPC trace of batch P1a
139 GPC trace of batch P2a
141 GPC trace of batch P3a
143 GPC trace of batch P4a
145 GPC trace of batch P5a
147 Storage modulus (G') of batch P6a (modified Methyl-P[nPrOzi$_{50}$-b-MeOx$_{50}$]-tert-butyl-piperazine-1-carboxylat)
149 Loss modulus (G') of batch P6a
151 Light microscope image of a printed constructs composed of orthogonal stacks of hydrogel strands
153 cell loaded constructs
157 results of FACS analysis on the influence of the printing process on the viability of NIH 3T3 fibroblasts
159 cells incorporated into the material and printed
161 cells incorporated into the material without further processing
163 untreated control cells

The invention claimed is:

1. A thermoresponsive hydrogel comprising an aqueous solution of a block copolymer having a general chemical structure of one of the following formulas:

$$[A]_n\text{-}[B]_m \text{ or } [B]_n\text{-}[A]_m$$

wherein block [A] of the block copolymer is chosen from the group consisting of 2-n-propyl-2-oxazine, 2-cyclopropyl-2-oxazine, and 2-butyl-2-oxazine, wherein block [B] of the block copolymer is chosen from the group consisting of 2-methyl-2-oxazoline and 2-ethyl-2-oxazoline, wherein n is in the range of 20 to 300, wherein m is in the range of 20 to 300, and wherein n and m have the same or approximately the same value, and wherein the block copolymer is at a concentration of at least 18 wt. % in the aqueous solution to form the thermoresponsive hydrogel.

2. The thermoresponsive hydrogel according to claim 1, wherein the block copolymer is prepared by a two-stage co-polymerization.

3. The thermoresponsive hydrogel according to claim 1, wherein the block copolymer has a general chemical structure of one of the following formulas:

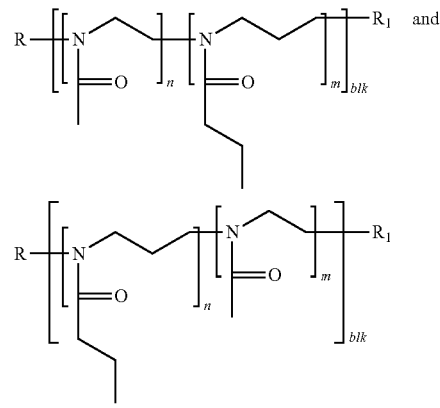

wherein R is an alkyl group and $R_1$ is a piperdine group, wherein n is in the range of 20 to 300, wherein m is in the range of 20 to 300, and wherein n and m have the same or approximately the same value.

4. The thermoresponsive hydrogel according to claim 1, wherein the block copolymer has a general chemical structure of the formula:

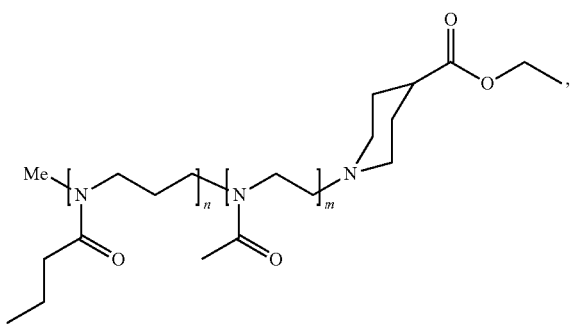

wherein n and m each have a value of 50.

5. The thermoresponsive hydrogel according to claim 1, wherein the block copolymer has a general chemical structure of the following formula:

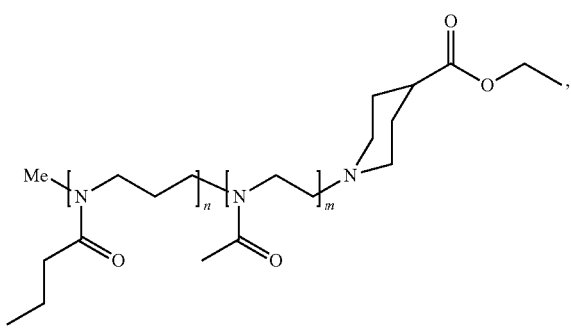

wherein n and m each have a value of 100.

6. The thermoresponsive hydrogel according to claim 1, wherein the block copolymer gels at a temperature above 10° C.

7. The thermoresponsive hydrogel according to claim 6, wherein the block copolymer gels at a temperature above 25° C.

8. The thermoresponsive hydrogel according to claim 7, wherein the block copolymer gels at a temperature above 30° C.

9. The thermoresponsive hydrogel according to claim 8, wherein the block copolymer gels at a temperature above 35° C.

10. A composition which comprises an active ingredient and the thermoresponsive hydrogel according to claim 1 as a carrier material for the active agent.

11. The composition according to claim 10, wherein the active agent is embedded in the carrier material.

12. The composition according to claim 11, wherein the carrier material is characterized by time-delayed release or distribution of the active ingredient.

13. A drug delivery system which comprises a drug or drugs and the thermoresponsive hydrogel according to claim 1 as a carrier material for the drug or drugs.

14. The drug delivery system of claim 13, wherein the carrier material is characterized by time-delayed release or distribution of the drug or drugs.

15. A composition which comprises cells and the thermoresponsive hydrogel according to claim 1 as a carrier material for the cells.

16. A composition which comprises one or more proteins and the thermoresponsive hydrogel according to claim 1 as a carrier material for the one or more proteins.

17. A block copolymer which has a general chemical structure of the formula:

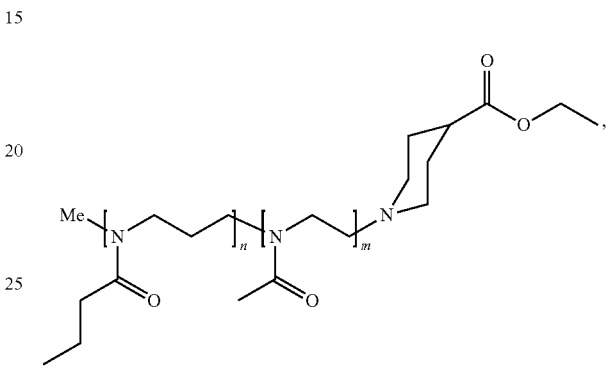

wherein n and m each have a value of 50.

18. A block copolymer which has a general chemical structure of the following formula:

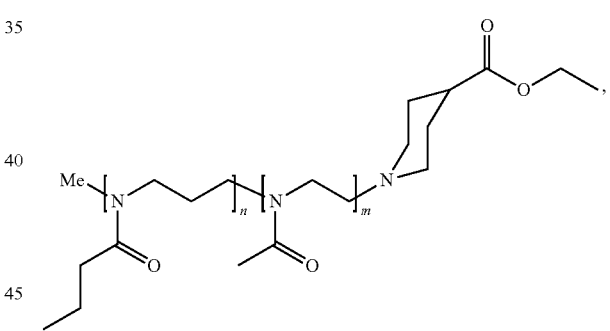

wherein n and m each have a value of 100.

19. The thermoresponsive hydrogel according to claim 1, further comprising a phosphate buffer saline.

20. The thermoresponsive hydrogel according to claim 1, further comprising one or more members selected from the group consisting of a drug, a protein, and cells.

* * * * *